(12) United States Patent
Longo et al.

(10) Patent No.: US 9,604,907 B2
(45) Date of Patent: Mar. 28, 2017

(54) METHODS OF FACILITATING NEURAL CELL SURVIVAL USING NON-PEPTIDE AND PEPTIDE BDNF NEUROTROPHIN MIMETICS

(71) Applicants: The University of North Carolina at Chapel Hill, Chapel Hill, NC (US); The Regents of the University of California, Oakland, CA (US); The United States of America as represented by the Department of Veterans Affairs, Washington, DC (US)

(72) Inventors: Frank M. Longo, Menlo Park, CA (US); Stephen M. Massa, Burlingame, CA (US)

(73) Assignees: The University of North Carolina at Chapel Hill, Chapel Hill, NC (US); The Regents of The University of California, Oakland, CA (US); The United States of America as represented by the Department of Veterans Affairs, Washington, DC (US)

( * ) Notice: Subject to any disclaimer, the term of this patent is extended or adjusted under 35 U.S.C. 154(b) by 138 days.

(21) Appl. No.: 14/165,090

(22) Filed: Jan. 27, 2014

(65) Prior Publication Data
US 2014/0200277 A1 Jul. 17, 2014

Related U.S. Application Data

(62) Division of application No. 11/449,381, filed on Jun. 8, 2006, now Pat. No. 8,686,045.

(60) Provisional application No. 60/688,767, filed on Jun. 8, 2005.

(51) Int. Cl.
| | | |
|---|---|---|
| *C07C 215/68* | (2006.01) |
| *A61K 31/40* | (2006.01) |
| *A61K 31/401* | (2006.01) |
| *A61K 31/4178* | (2006.01) |
| *A61K 38/18* | (2006.01) |
| *C07K 5/097* | (2006.01) |
| *C07K 5/107* | (2006.01) |

(52) U.S. Cl.
CPC ............ *C07C 215/68* (2013.01); *A61K 31/40* (2013.01); *A61K 31/401* (2013.01); *A61K 31/4178* (2013.01); *A61K 38/185* (2013.01); *C07K 5/0823* (2013.01); *C07K 5/1016* (2013.01)

(58) Field of Classification Search
CPC .................................................. C07C 215/68
See application file for complete search history.

(56) References Cited

U.S. PATENT DOCUMENTS

| | | | |
|---|---|---|---|
| 3,953,416 | A | 4/1976 | Folkers et al. |
| 4,552,864 | A | 11/1985 | Antoni et al. |
| 5,321,029 | A | 6/1994 | Maschler et al. |
| 5,958,875 | A | 9/1999 | Longo et al. |
| 6,017,878 | A | 1/2000 | Saragovi et al. |
| 6,583,148 | B1 | 6/2003 | Kelley et al. |
| 6,780,580 | B2 | 8/2004 | LeCluyse et al. |
| 6,881,719 | B2 | 4/2005 | Saragovi et al. |
| 8,686,045 | B2 | 4/2014 | Longo et al. |
| 2003/0211982 | A1 | 11/2003 | Saragovi et al. |
| 2006/0246072 | A1 | 11/2006 | Longo et al. |
| 2007/0060526 | A1 | 3/2007 | Longo et al. |

FOREIGN PATENT DOCUMENTS

| | | |
|---|---|---|
| DE | 23 11 786 | 9/1973 |
| DE | 23 43 037 | 3/1975 |
| EP | 1 008 656 | 6/2000 |
| EP | 2 526 942 | 11/2012 |
| GB | 1 323 247 | 7/1973 |
| WO | WO96/16980 | 6/1996 |
| WO | WO00/06137 | 2/2000 |
| WO | WO02/060867 | 8/2002 |
| WO | WO2004/028466 | 4/2004 |
| WO | WO2006/113097 | 10/2006 |
| WO | WO2006/133353 | 12/2006 |

OTHER PUBLICATIONS

Leburn et al. "Brain-derived neurotrophic factor (BDNF) and food intake regulation: A minireview," Autonomic Neuroscience: Basic and Clinical, 2006, vol. 126-127, pp. 30-38.*
He et al. "Conditional Deletion of TrkB but Not BDNF Prevents Epileptogenesis in the Kindling Model" Neuron, 2004, vol. 43, pp. 31-42.*
Wisse et al. "The skinny on neurotrophins" Nature Neuroscience, 2003, vol. 6, No. 7, pp. 655-656.*
Nakagawa et al. "Antiobesity and antidiabetic effects of brain-derived neurotrophic factor in rodent models of leptin resistance" International Jurnal of Obesity, 2003, vol. 27, pp. 557-565.*
Desmet et al. The neurotrophic receptor TrkB: a drug target in anti-cancer therapy?, Cell. Mol. Life Sci., 2006, vol. 63, pp. 755-759.*
Schechter et al. "Innovative Approaches for the Development of Antidepressant Drugs: Current and Future Strategies" NeuroRx: The Journal of the American Society for Experimental NeuroThrapeutics, 2005, vol. 2, pp. 590-611.*

(Continued)

*Primary Examiner* — Kendra D Carter
(74) *Attorney, Agent, or Firm* — Jenkins, Wilson, Taylor & Hunt

(57) ABSTRACT

Methods and compounds for treating neurological and other disorders are provided. Included is the administering to a subject in need thereof an effective amount of a compound having binding and/or modulation specificity for a TrkB receptor molecule.

11 Claims, 8 Drawing Sheets

(56) References Cited

OTHER PUBLICATIONS

Saragovi et al. "Small Molecule Peptidomimetic Ligands of Neurotrophin Receptors, Identifying Binding Sites, Activation Sites and Regulatory Sites" Current Pharmaceutical Design, 2002, vol. 8, No. 24, pp. 2201-2216.*
O'Leary et al. "Design of Potent Peptide Mimetics of Brain-derived Neurotrophic Factor", The Journal of Biological Chemistry, 2003, vol. 278, No. 28, pp. 25738-25744.*
Seebach et al. "Effects of BDNF and NT-3 on Develoopment of Ia/Motoneuron Functional Connectivity in Neuonatal Rats", J Neurophysiol, 1999, pp. 2398-2405.*
Pollack et al. "Small Molecule Trk REceptor Agonists and Other Neurotrophic Factor Mimetics", Current Drug Targets-CNS and Neurological Disorders, 2002, vol. 1, pp. 59-80.*
J. G. G Cannon Chapter Nineteen in Burgers Medicinal Chemistry and Drug Discovery, Fifth Edition, vol. I: Principles and Practice, Wiley-Interscience 1995, pp. 783-802, 784.*
Decision to Grant corresponding to European Patent Application No. 12 169 982.1-1408 dated Oct. 7, 2015.
"The BDNF Study Group," Neurology. vol. 52 pp. 1427-1433 (1999).
Beattie et al., Neuron. vol. 36 pp. 375-386 (2002).
Canals et al., J. Neurosci. vol. 24 pp. 7727-7739 (2004).
Cannon, "Burger's Medicinal Chemistry and Drug Discovery," Chapter 19, 5th Edition. vol. I: Principles and Practice, Wiley-Interscience. pp. 783-802 (1995).
Carlson et al., "Developing a dynamic pharmacophore model for HIV-1 integrase," Journal of Medicinal Chemistry. vol. 43 pp. 2100-2114 (2000).
Carter et al., Science. vol. 272 pp. 542-545 (2002).
Casaccia-Bonnefil et al., Nature. vol. 386 pp. 716-719 (1996).
Cattaneo et al., Nat. Rev. Neurosci. vol. 6 pp. 919-930 (2005).
Chaturvedi et al., "Topochemically Related Hormone Structures. Synthesis of Partial Retro-Inverso Analogs of LH-RH," International Journal of Peptide and Protein Research. vol. 17, No. 1 pp. 72-88 (1981).
Chorev at al., "Novel Partially Modified Retro-Inversion Analogs of Biologically Active Peptides," Proceedings of the American Peptide Symposium. pp. 455-458 (Jan. 1, 1979).
Dahlgren, J. Biol. Chem. vol. 277 pp. 32046-32053 (2002).
Dechant, G., and Barde, Y., "The neurotrophin receptor $p75^{NTR}$: novel functions and implications for diseases of the nervous system," Nature Neuroscience. vol. 5, No. 11 pp. 1131-1136 (2002).
Decision to Grant corresponding to Japanese Patent Application No. 2008-515915 dated Jan. 14, 2014.
Desmet, C.J., and Peeper, D.S., The neurotrophic receptor TrkB: a drug target in anti-cancer therapy? Cellular and Molecular Life Sciences. vol. 63 pp. 755-759 (2006).
Dluzen, Neuroscience. vol. 128 pp. 201-208 (2004).
Elliot et al., Eur. J. Neurosci. vol. 22 pp. 1081-1089 (2005).
Elmore et al., "Further Characterization of the Substrate Specificity of a TRH Hdryolsing Pyroglutamate Aminopeptidase from Guinea-Pig Brain," Neuropeptides. vol. 15 pp. 31-36 (1990).
Endres et al., "Ischemic Brain Damage in Mice After Selectively Modifying BDNF or NT4 Gene Expression," Journal of Cerebral Blood Flow and Metabolism. vol. 20 pp. 139-144 (2000).
Extended European Search Report corresponding to European Patent Application No. 06 784 665.9-2404 dated Mar. 1, 2010.
Extended European Search Report corresponding to European Patent Application No. 12 169 982.1-1408 dated May 28, 2013.
Extended European Search Report corresponding to European Patent Application No. 12 169 984.7-1408 dated Jun. 17, 2013.
Fahnestock et al., Mol. Cell. Neurosci. vol. 18 pp. 210-220 (2001).
Fletcher, J.M., and Hughes, R.A., "Novel monocyclic and bicyclic loop mimetics of brain-derived neurotrophic factor," Journal of Peptide Science. vol. 12 pp. 515-524 (2006).
Foehr et al., J. Neurosci. Res. vol. 73 pp. 7556-7563 (2003).
Fumagalli et al., "The expanding role of BDNF: a therapeutic target of Alzheimer's disease?" The Pharmacogenomics Journal. vol. 6 pp. 8-15 (2005).
Gentry et al., J. Biol. Chem. vol. 275 pp. 7558-7565 (2000).
Gielen et al., Scan. J. Imm. vol. 57 pp. 493-497 (2003).
Guillin et al., Eur. J. Pharm. vol. 480 pp. 89-95 (2003).
Harrington et al., J. Neurosci. vol. 22 pp. 156-166 (2002).
Harrington et al., PNAS. vol. 101. pp. 6226-6230 (2004).
He et al., "Conditional Deletion of TrkB but Not BDNF Prevents Epileptogenesis in the Kindling Model," Neuron. vol. 43 pp. 31-42 (2004).
He, X.L., and Garcia, K.C., Science. vol. 304 pp. 870-875 (2004).
Huang et al., J. Biol. Chem. vol. 274 pp. 36707-36714 (1999).
Huang, E.J., and Reichardt, L.F., Annu. Rev. Biochem. vol. 72 pp. 609-642 (2003).
Hunt et al., "Sequence Analysis of Polypeptides by Collision Activated Dissociation on a Triple Quadrupole Mass Spectrometer," Biomedical Spectrometry. vol. 8, No. 9 pp. 397-408 (1981).
Inetrosa et al., "Peroxisome proliferator-activated receptor γ is expressed in hippocampal neurons and its activation prevents β-amyloid nerodegeneration: role of Wnt signaling," Experimental Cell Research. vol. 304 pp. 91-104 (2005).
International Search Report and the Written Opinion of the International Searching Authority, or the Declaration corresponding to International Patent Application No. PCT/US2006/011985 dated Dec. 28, 2006.
Interview Summary corresponding to U.S. Appl. No. 11/449,381 dated Jun. 30, 2011.
Interview Summary corresponding to U.S. Appl. No. 11/449,381 dated Sep. 14, 2012.
Kells et al., "AAV-Mediated Gene Delivery of BDNF or GDNF is Neuroprotective in a Model of Huntington Disease," vol. 9, No. 5 pp. 682-688 (2004).
Kermani et al., J. Clin. Invest. vol. 115 pp. 653-663 (2005).
Kline et al., "Exogenous Brain-Derived Neurotrophic Factor Rescues Synaptic Dysfunction in *Mecp2*-Null Mice," The Journal of Neuroscience. vol. 30, No. 15 pp. 5303-5310 (2010).
Kode et al., J. Neurotrauma. vol. 21 pp. 329-337 (2004).
Koyama, R., and Ikegaya, Y., The Neuroscientist. vol. 11 pp. 282-287 (2005).
Lachyankar et al., J. Neurosci. Res. vol. 71 pp. 157-172 (2003).
Lad, S.P., and Neet, K.E., J. Neurosci. Res. vol. 73 pp. 614-626 (2003).
Lebrun et al., "Brain-derived neurotrophic factor (BDNF) and food intake regulation: A minireview," Autonomic Neuroscience: Basic and Clinical. vol. 126-127 pp. 30-38 (2006).
Lee et al., Cell. vol. 69 pp. 737-749 (1992).
Lee et al., Science. vol. 294 pp. 1945-1948 (2001).
Li et al., "Target for preventing epilepsy following critical injury," Neuroscience Letters, vol. 497, No. 3 pp. 172-176 (2011).
Lin et al., J. Biol. Chem. vol. 270 pp. 14255-14258 (1995).
Longo et al., "Neurotrophin Small Molecule Mimetics: Candidate Therapeutic Agents for Neurological Disorders," Current Medicinal Chemistry—Central Nervous System Agents. vol. 5, No. 1, pp. 29-41 (2005).
Longo et al., "Neurotrophin-based strategies for neuroprotection," Journal of Alzheimer's Disease. vol. 6 pp. S13-S17 (2004).
Longo, F.M., and Massa, S.M., "Small Molecule Modulation of p75 Neurotrophin Receptor Functions," CNS & Neurological Disorderes—Drug Targets. vol. 7 pp. 63-70 (2008).
Longo et al., J. Neurosci. Res. vol. 48 pp. 1-17 (1997).
Longo et al., J. Neurosci. Res. vol. 55 pp. 230-237 (1999).
MacLellan et al., "A Critical Threshold of Rehabilitation Involving Brain-Derived Neurotrophic Factor is Required for Poststroke Recovery," Neurorehabilitation and Neural Repair. vol. 25, No. 6 pp. 1-9 (2011).
Malcangio, M., and Lessmann, V., "A common thread for pain and memory synapses? Brain-derived neurotrophic factor and trkB receptors," TRENDS in Pharmacological Sciences. vol. 24, No. 3 pp. 116-121 (2003).
Maliartchouk et al., J. Biol. Chem. vol. 275 pp. 9946-9956 (2000).
Mamidipudi et al., J. Biol. Chem. vol. 277 pp. 28010-28018 (2002).
Marche et al., "Conformational Characteristics of Luliberin Circular Dichoroism and Fluorescence Studies," Biochemistry. vol. 15, No. 26 pp. 5730-5737 (1976).

(56) References Cited

OTHER PUBLICATIONS

Masoikiewicz et al., "Synthesis of [DSer(tBu)6, desGly19]GnRH-Et without side-chain protection," Polish Journal of Chemistry. vol. 69, No. 1 pp. 674-680 (1995).
Massa et al., "Alzheimer's Therapeutics," Journal of Molecular Neuroscience. vol. 19 pp. 107-111 (2002).
Massa et al., "Alzheimer's Therapeutics: Neurotrophin Domain Small Molecule Mimetics," Journal of Molecular Neuroscience. vol. 20 pp. 323-326 (2003).
Massa et al., "Small, Nonpeptode $p75^{NTR}$ Ligands Induce Survival Signaling and Inhibit proNGF-Induced Death," The Journal of Neuroscience. vol. 26, No. 20 pp. 5288-5300 (2006).
Massa et al., "Small Molecule BDNF mimetics activate TrkB signalling and prevent neuronal degeneration in rodents," The Journal of Clinical Investigation. vol. 120, No. 5 pp. 1774-1785 (2010).
McGuinness, S.L., and Shepherd, R.K., Otol. Neurotol. vol. 26 pp. 1064-1072 (2005).
Mecklenburg et al., "LH-releasing activity of p-Glu-His-Trp-NH2 and p-Glu-His-Trp," Endocrinology. vol. 93, No. 4 pp. 993-997 (1973).
Michaelis et al., J. Pharm. Exp. Ther. vol. 312 pp. 659-668 (2005).
Nakagawa et al., "Antiobesity and antidiabetic effects on brain-derived neurotrophic factor in rodent models of leptin resistance," International Journal of Obesity. vol. 27 pp. 557-565 (2003).
Nomura et al., Neurosci. vol. 136 pp. 161-169 (2005).
Nosheny et al., "Brain derived Neurotrophic Factor as Prototype Neuroprotective Factor Against HIV-1-associated Neuronal Degeneration," Neurotoxicity Research. vol. 8, Nos. 1-2 pp. 187-198 (2005).
Notice of Allowance corresponding to U.S. Appl. No. 11/449,381 dated Oct. 25, 2013.
Noting of Loss of Rights Pursuant to Rule 112(1) EPC corresponding to European Patent Application No. 06784665.9 dated Jul. 24, 2012.
Notification Concerning Transmittal of International Preliminary Report on Patentability (Chapter I of the Patent Cooperation Treaty) corresponding to International Patent Application No. PCT/US2006/011985 dated Oct. 25, 2007.
Notification Concerning Transmittal of International Preliminary Report on Patentability (Chapter I of the Patent Cooperation Treaty) corresponding to International Patent Application No. PCT/US2006/022268 dated Apr. 9, 2009.
Nykjaer et al., Curr. Opin. Neurobiol. vol. 15 pp. 49-57 (2005).
Nykjaer et al., Nature. vol. 427 pp. 843-848 (2004).
O'Leary, P.D., and Hughes, R.A., "Design of Potent Peptide Mimetics of Brain-derived Neurotrophic Factor," The Journal of Biological Chemistry. vol. 27, No. 28 pp. 25738-25744 (2003).
Official Action corresponding to European Patent Application No. 06 784 665.9-2404 dated May 21, 2010.
Official Action corresponding to European Patent Application No. 06 784 665.9-2404 dated Feb. 7, 2012.
Official Action corresponding to Japanese Patent Application No. 2008-515915 dated Jan. 10, 2012.
Official Action corresponding to Japanese Patent Application No. 2008-515915 dated Jan. 31, 2013.
Official Action corresponding to U.S. Appl. No. 11/396,936 dated Feb. 26, 2009.
Official Action corresponding to U.S. Appl. No. 11/396,936 dated May 27, 2009.
Official Action corresponding to U.S. Appl. No. 11/396,936 dated Aug. 25, 2009.
Official Action corresponding to U.S. Appl. No. 11/449,381 dated Nov. 25, 2009.
Official Action corresponding to U.S. Appl. No. 11/449,381 dated Aug. 18, 2010.
Official Action corresponding to U.S. Appl. No. 11/449,381 dated Mar. 1, 2011.
Official Action corresponding to U.S. Appl. No. 11/449,381 dated May 3, 2012.
Partial European Search Report corresponding to European Patent Application No. 12 169 982.1-1408 dated Feb. 12, 2013.
Partial European Search Report correspoding to European Patent Application No. 12 169 984.7-1408 / 2526942 dated Feb. 13, 2013.
Partridge, Adv. Exp. Med. Bio. vol. 513 pp. 397-430 (2002).
Patani et al., "Bioisosterism: A Rational Approach in Drug Design," Chemical Reviews. vol. 96, No. 8 pp. 3147-3176 (1996).
Pérez-Navarro et al., "Brain-Derived Neurotrophic Factor, Neurotrophin-3 and Neurotrophin-4/5 Prevent the Death of Striatal Projection Neurons in a Rodent Model of Huntington's Disease," Journal of Neurochemistry. vol. 75 pp. 2190-2199 (2000).
Pérez-Navarro et al., "Neurturin Protects Striatal Projection Neurons but No Interneurons in a Rat Model of Huntington's Disease," Neuroscience. vol. 98, No. 1 pp. 89-96 (2000).
Pettit, G.R., and Smith, T.H., "Structural Biochemistry 13, Synthesis of Luteinizing Hormone Releasing Hormone Modification 8 Tryptophan Substituted Luteinizing Hormone Releasing Hormone," Journal of Pharmaceutical Sciences. vol. 68, No. 8 pp. 1013-1015 (1979).
Podulso, J.F., and Curran, G.L., Brain Res. Mol. Brain Res. vol. 36 pp. 280-286 (1996).
Pollack, S.J., and Harper, S.J., "Small Molecule Trk Receptor Agonists and Other Neurotrophic Factor Mimetics," Current Drug Targets—CNS & Neurological Disorders. vol. 1 No. pp. 59-80 (2002).
Pesgraves et al., "Terminally Differentiated SH-SY5Y Cells Provide a Model System for Studying Neuroprotective Effects of Dopamine Agonists," Neurotoxicity Research. vol. 5, No. 8 pp. 579-598 (2004).
Presraves et al., Exp. Neurol. vol. 190 pp. 157-170 (2004).
Qian et al., "Novel Agonist Monoclonal Antibodies Activate TrkB Receptors and Demonstrate Potent Neurotrophic Activities," The Journal of Neuroscience. vol. 26, No. 37 pp. 9394-9403 (2006).
Root-Bernstein et al., "Serotonin Binding Sites I. Structures of Sites on Myelin Basic Protein, LHRH, MSH, ACTH, interferon, serum albumin, ovalbumin and red pigment concentrating hormone," Brain Research Bulletin. vol. 12, No. 4 pp. 425-436 (1984).
Roux et al., J. Biol. Chem. vol. 276 pp. 23097-23104 (2001).
Sakurai et al., J. Biol. Chem. vol. 274 pp. 30353-30356 (1999).
Salehi et al., Neuron. vol. 27 pp. 279-288 (2000).
Saltzman et al., Pharm. Res. vol. 16 pp. 232-240 (1999).
Saragovi et al., Current Pharmaceutical Design. vol. 8, No. 24 pp. 2201-2216 (2002).
Schabitz et al., Stroke. vol. 35 pp. 992-997 (2004).
Schally et al., "Inhibition of sham feeding-induced gastric secretion and serum hormonal responses by analogs of (pyro)Glu-His-Gly-OH," Proceedings of the Society for Experimental Biology and Medicine. vol. 170, No. 3 pp. 264-272 (1982).
Schally et al., "Luteinizing hormone-releasing hormone (LH-RH) activity of some synthetic polypeptides. I. Fragments Shorter Than Decapeptide," Biochemical and Biophysical Research. vol. 48, No. 2 pp. 366-375 (1972).
Schechter et al., "Innovative Approaches for the Development of Antidepressant Drugs: Current and Future Strategies," NeuroRx. vol. 2, No. 4 pp. 590-611 (2005).
Schellenberger et al., "Chymotrypsin-Catalyzed Fragment Coupling Synthesis of D Phenylalanine-6 GNRH," Tetrahedron Letters. vol. 31, No. 50 pp. 7305-7306 (1990).
Seebach et al., "Effects of BDNF and NT-3 on Development of Ia/Motoneuron Functional Connectivity in Neonatal Rats," J. Neurophysiol. vol. 81 pp. 2398-2405 (1999).
Simmons et al., "A small molecule, non-peptide TrkB ligand reduces motor impariment and neuropathology in R6/2 mouse model of Huntington's Disease," Poster, Stanford School of Medicine (1 page).
Stadelmann et al., Brain. vol. 125 pp. 75-85 (2002).
Sun, Y.E., and Wu, H., Neuron. vol. 49 pp. 321-323 (2006).
Tapley et al., "K252A is a Selective Inhibitor of the Tyrosine Protein Kinase Activity of the TRK Family of Oncogenes and Neurotrophin Receptors," Oncogene. vol. 7. No. 2 pp. 371-381 (1992).

(56) References Cited

OTHER PUBLICATIONS

Thoenen, H., and Sendtner, M., "Neurotrophins: from enthusiastic expectations through sobering experiences to rational therapeutic approaches," Nature Neuroscience Supplement. vol. 5 pp. 1046-1050 (2002).
Vogelin et al., The Journal of Experimental Neurology. (Feb. 15, 2006).
Walsh et al., J. Neurosci. vol. 19 pp. 258-273 (1999).
Wang et al., J. Neurosci. Res. vol. 60 pp. 587-593 (2000).
Watabe et al., Neuropath. vol. 25 pp. 371-380 (2005).
Wilk et al., "Pyroglutamyl Peptidase II, A Thyrotropin Releasing Hormone Degrading Enzyme: Purification and Specificity Studies of the Rabbit Brain Enzyme," Neurochemistry International. vol. 15, No. 1 pp. 81-89 (1989).
Williams et al., "Overcoming the Inhibitors of Myelin with a Novel Neurotrophin Strategy," Journal of Biological Chemistry. vol. 280, No. 7 pp. 5862-5869 (2005).
Wisse, B.E., and Schwartz, M.W., "The skinny on neurotrophins," Nature Neuroscience. vol. 6, No. 7 pp. 655-656 (2003).
Wu, "Neuroprotection in Experimental Stroke with Targeted Neurotrophins," NeuroRx. vol. 2, No. 1 pp. 120-128 (2005).
Yabe et al., "Synthesis and Biological Activity of Luteinizing Hormone Releasing Hormone Analogs Substituted by Alkyl Trytophans at Position 3," Chemical and Pharmaceutical Bulletin. vol. 27, No. 8 pp. 1907-1911 (1979).
Yang et al., J. Neurosci. vol. 23 pp. 3353-3363 (2003).
Yankner et al., PNAS. vol. 87 pp. 9020-9023 (1990).
Yoon et al., J. Neurosci. vol. 18 pp. 3273-3281 (1998).
Zhang et al., J. Neurosci. vol. 23 pp. 7385-7394 (2003).
Zhou et al., J. Neurochem. vol. 65 pp. 1146-1156 (1995).
Zhou et al., PNAS. vol. 91 pp. 3824-3828 (1994).
Official Action corresponding to European Patent Application No. 12 169 984.7-1408 dated Jul. 4, 2014.
Official Action corresponding to European Patent Application No. 12 169 984.7-1408 dated Feb. 3, 2015.
Official Action corresponding to European Patent Application No. 12 169 982.1-1408 dated Jul. 4, 2014.
Official Action corresponding to European Patent Application No. 12 169 982.1-1408 dated Feb. 3, 2015.
Decision to grant a European patent pursuant to Article 79 (1) EPC for European Patent Application No. 12169982.1 dated Feb. 18, 2016.
English abstract from CAS for Oelssner W., "Pharmacology of methylxanthine derivatives. I. Theophylline derivatives substituted in the 7-position," Pharmazie. vol. 16 pp. 1-2 (1961).
Summons to attend Oral Proceedings Pursuant to Rule 115(1) EPC corresponding to European Patent Application No. 12 169 984.7-1408 dated Jun. 28, 2016.

\* cited by examiner

METHODS OF FACILITATING NEURAL CELL SURVIVAL USING NON-PEPTIDE AND PEPTIDE BDNF NEUROTROPHIN MIMETICS

CROSS REFERENCE TO RELATED APPLICATIONS

This application is a Divisional of U.S. patent application Ser. No. 11/449,381, filed Jun. 8, 2006, which is based on and claims priority to U.S. Provisional Application Ser. No. 60/688,767, filed Jun. 8, 2005, each of which is herein incorporated by reference in its entirety.

GRANT STATEMENT

This invention was made with government support under Grant No. NS030687 awarded by the National Institutes of Health. The government has certain rights in the invention.

TECHNICAL FIELD

The presently disclosed subject matter generally relates to the treatment of disorders in a subject, including but not limited to neurological disorders. More particularly, the methods of the presently disclosed subject matter relate to administering to a subject an effective amount of a compound having binding and/or modulation specificity for the TrkB receptor molecule to treat a disorder in the subject.

TABLE OF ABBREVIATIONS

| | |
|---|---|
| 2D | two-dimensional |
| 3D | three-dimensional |
| Aβ | amyloid-β |
| Ab | antibody |
| AD | Alzheimer's disease |
| ALS | amyotrophic lateral sclerosis |
| BCA | bicinchoninic acid |
| BDNF | brain-derived neurotrophic factor |
| b.i.d. | twice daily |
| cm | centimeter |
| d | day |
| D | Dalton |
| DMEM | Dulbecco's Modified Eagle Media |
| ECL | electrogenerated chemiluminescence |
| EDTA | ethylenediamine tetraacetic acid |
| ELISA | Enzyme Linked ImmunoSorbent Assay |
| ERK | extracellular signal-regulated protein kinase |
| FBS | fetal bovine serum |
| g | gram |
| h | hour |
| HBA | hydrogen bond acceptor |
| HBD | hydrogen bond donor |
| HD | Huntington's disease |
| HEPES | 4-2-hydroxyethyl-1-piperazineethanesulfonic acid |
| HRP | horseradish peroxidase |
| IgG | Immunoglobin G |
| IP | Intraperitoneal |
| IV | intravenous |
| $K^{32}$ | lysine residue number 32 |
| kcal | kilocalorie |
| kg | kilogram |
| MBP | myelin basic protein |
| mg | milligram |
| min | minute |
| ml | milliliter |
| mM | millimolar |
| mol | mole |
| MTT | 3-(4,5-dimethylthiazol-2-yl)-2,5-diphenyltetrazolium bromide |
| MW | molecular weight |
| NaCl | sodium chloride |
| ng | nanogram |
| nM | nanomolar |
| NS | not significant |
| NMR | nuclear magnetic resonance |
| NGF | nerve growth factor |
| nM | nanomolar |
| P | probability |
| $p75^{NTR}$ | p75 neurotrophin receptor |
| PBS | phosphate-buffered saline |
| PD | Parkinson's disease |
| pmol | picomole |
| PMSF | phenylmethylsulfonyl fluoride |
| PO | per os (by mouth) |
| pro-NGF | unprocessed precursor of NGF |
| PVDF | Polyvinylidine Difluroide |
| SDS | sodium dodecyl sulfate |
| SE | standard error |
| s.e.m. | standard error of measurement |
| Tris | 2-Amino-2-(hydroxymethyl)-1,3-propanediol |
| TUNEL | Terminal deoxynucleotidyl transferase-mediated deoxyuridine triphosphate nick-end labeling |
| μg | microgram |
| μl | microliter |
| μM | micromolar |
| % | percent |
| °C. | degrees Celsius |
| ≥ | greater than or equal to |
| > | greater than |
| ≤ | less than or equal to |
| < | less than |

BACKGROUND

Neurotrophins are polypeptides that play a role in the development, function, and/or survival of certain cells, including neurons. The death or dysfunction of neurons has been directly implicated in a number of neurological disorders. It has been suggested that alterations in neurotrophin localization, expression levels of neurotrophins, and/or expression levels of the receptors that bind neurotrophins are linked to neuronal degeneration or dysfunction. This degeneration or dysfunction can occur in the neurological disorders Alzheimer's, Parkinson's, Huntington's disease and amyotrophic lateral sclerosis (ALS), among others. Neurotrophins also mediate fundamental mechanisms relevant to non-neurological disorders including for example depression, obesity, and ischemic conditions of peripheral tissues.

A variety of neurotrophins have been identified, including Nerve Growth Factor (NGF), Neurotrophin-3 (NT-3), Neurotrophin-4/5 (NT-4/5), Neurotrophin 6 (NT-6) and Brain Derived Neurotrophic Factor (BDNF). Neurotrophins are found in both precursor form, known as pro-neurotrophins, and in mature form. The mature forms are proteins of about 120 amino acids in length that exist in physiological states as stable, non-covalent approximately 25 kDa homodimers. Each neurotrophin monomer includes three solvent-exposed β-hairpin loops, referred to as loops 1, 2, and 4 that exhibit relatively high degrees of amino acid conservation across the neurotrophin family.

Mature neurotrophins bind preferentially to the receptors Trk and $p75^{NTR}$ while pro-neurotrophins, which contain an N-terminal domain proteolytically removed in mature forms, interact principally with the $p75^{NTR}$ receptor and through their N-terminal domains, with the sorting receptor sortilin (Fahnestock, M., Michalski, B., Xu, B., Coughlin, M. D. (2001) *Mol Cell Neurosci* 18, 210-220; Harrington, A. W. et al. (2004) *Proc Natl Acad Sci USA* 101, 6226-6230; Nykjaer, A. et al., (2004) *Nature* 427, 843-848). The $p75^{NTR}$ receptor interacts with Trks and modulates Trk signaling, but is also independently coupled to several signaling systems, including pro-survival signals, IRAK/TRAF6/NFκB, PI3/AKT, and pro-apoptotic signals, NRAGE/JNK (Mamidipudi, V., Li, X., Wooten, M. W. (2002) *J Biol Chem* 277, 28010-28018; Roux, P. P., Bhakar, A. L., Kennedy, T. E., Barker, P. A. (2001) *J Biol Chem* 276, 23097-23104; Salehi, A. H., et al. (2000) *Neuron* 27, 279-288).

Depending on the operative ligands, co-expression of Trk or other receptors, and expression of downstream signaling elements, $p75^{NTR}$ promotes cell survival or death. proNGF induces death of superior cervical ganglion neurons and oligodendrocytes through $p75^{NTR}$, and its comitant binding to $p75^{NTR}$ and sortilin has been shown to activate cell death pathways (Nykjaer, A. et al., (2004) *Nature* 427, 843-848; Lee, R., Kermani, P., Teng, K. K., Hempstead, B. L. (2001) *Science* 294, 1945-1948; Beattie, M. S. et al. (2002) *Neuron* 36, 375-386).

When administered for therapeutic use, neurotrophins exhibit suboptimal pharmacological properties, including poor stability with low serum half lives, likely poor oral bioavailability, and restricted central nervous system penetration (Podulso, J. F., Curran, G. L. (1996) *Brain Res Mol Brain Res* 36, 280-286; Saltzman, W. M., Mak, M. W., Mahoney, M. J., Duenas, E. T., Cleland, J. L. (1999) *Pharm Res* 16, 232-240; Partridge, W. M. (2002) *Adv Exp Med Bio* 513, 397-430). Additionally, the highly pleiotropic effects of neurotrophins achieved through action of the triple receptor signaling network increases the chances of adverse effects.

Unfortunately, technical and ethical considerations have thus far hampered the development of therapeutic agents based upon neurotrophins. For example, it is technically difficult to produce sufficient quantities of pure neurotrophins using recombinant DNA techniques. Additionally, although it is possible to utilize human fetal cells to produce neurotrophins, the ethical ramifications raised by the use of such cells (typically obtained from an aborted fetus) have all but prevented the utilization of this approach.

Previous studies have described the creation of synthetic peptides corresponding to various domains of the BDNF protein that are capable of achieving the BDNF effect of promoting neurite outgrowth (O'Leary and Hughes, 2003; Williams et al., 2005; Fletcher and Hughes, 2006). While it is not known if these synthetic BDNF peptides actually activate the TrkB receptor or whether they achieve their neurotrophic effects by a non-TrkB mechanism, these peptides are too large (approximately 2000 MW) to constitute actual medicinal compounds.

Accordingly, there is an unmet need in the art for the development of small molecule (for example, <500 MW, characteristic of successful drugs) non-peptidyl or peptide agents based upon neurotrophins for use in the treatment of disorders. In particular, there is a need to identify small molecules that mimic key regions of neurotrophin proteins and have the ability to activate the TrkB receptor. There is further a need for small molecules that target TrkB receptors to avoid or minimize potentially deleterious interactions with the $p75^{NTR}$ and sortilin receptors.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

Disclosed herein are methods of treating a disorder in a subject, including both neurological and non-neurological disorders, comprising administering to the subject an effective amount of a small molecule compound having binding and/or modulation specificity for a TrkB receptor molecule.

In some embodiments, the disorder is selected from the group consisting of Alzheimer's disease, Huntington's disease, amyotrophic lateral sclerosis, Rett syndrome, epilepsy, Parkinson's disease, spinal cord injury, stroke, hypoxia, ischemia, brain injury, diabetic neuropathy, peripheral neuropathy, nerve transplantation complications, motor neuron disease, multiple sclerosis, HIV dementia, peripheral nerve injury, hearing loss, depression, obesity, metabolic syndrome, pain, cancer, and conditions involving degeneration or dysfunction of cells expressing TrkB.

In some embodiments, the subject is a human subject.

Also disclosed herein are methods of facilitating neural cell survival or promoting neural function comprising treating a neural cell with a compound having the ability to specifically bind and/or modulate the activity of a TrkB receptor molecule.

Additionally disclosed herein are compounds having binding and/or modulation specificity for a TrkB receptor molecule.

In some embodiments, the compound having binding and/or modulation specificity for a TrkB receptor molecule is a mimetic of a BNDF β-turn loop.

In some embodiments, the compound comprises a pharmacophore substantially identical to the pharmacophore illustrated in FIG. 1.

In some embodiments, the compound is a small molecule or small peptide.

In some embodiments, the BNDF β-turn loop is loop 2.

In some embodiments, the loop 2 BDNF mimetic compound has a structure of Formula (I):

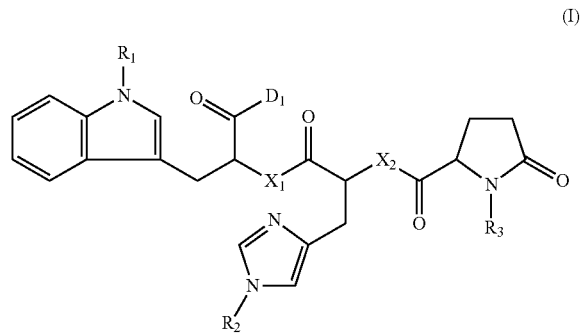

wherein:
$R_1$, $R_2$, and $R_3$ are independently selected from the group consisting of H, alkyl, aryl, aralkyl, acyl, alkoxycarbonyl, aryloxycarbonyl, aralkoxycarbonyl, carbamoyl, alkylcarbamoyl, and dialkylcarbamoyl;
$X_1$ and $X_2$ are independently selected from $CH_2$ and $NR_4$, wherein $R_4$ is selected from H, alkyl, aralkyl, and aryl; and
$D_1$ is selected from the group consisting of H, alkyl, aryl, aralkyl, hydroxyl, alkoxyl, aryloxyl, aralkoxyl, and

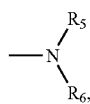

wherein $R_5$ and $R_6$ are H, alkyl, aralkyl, or aryl;
or a pharmaceutically acceptable salt.

In some embodiments, the compound of Formula (I) is

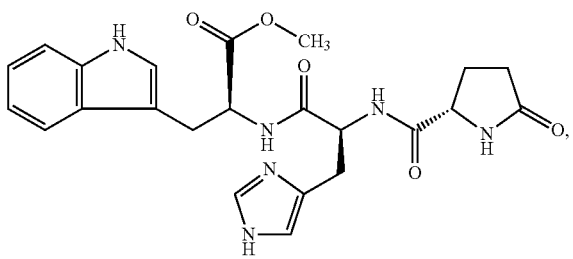 [SMILES: COC(=O)[C@H](Cc1c[nH]c2ccccc12)NC(=O)[C@H](Cc1c[nH]cn1)NC(=O)[C@@H]1CCC(=O)N1]

or a stereoisomer thereof.

In some embodiments, the loop 2 BDNF mimetic compound has a structure of Formula (II):

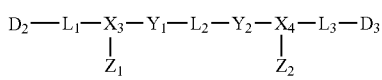

wherein:
- $L_1$ and $L_3$ are independently selected from the group consisting of $C_1$-$C_5$ alkylene, arylene, aralkylene, and substituted arylene;
- $L_2$ is selected from the group consisting of $C_1$-$C_5$ alkylene, arylene, aralkylene, substituted arylene,

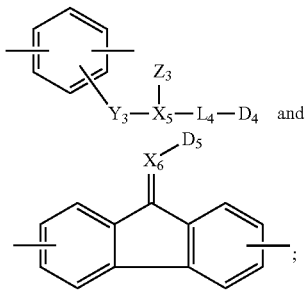

- $L_4$ is $C_1$-$C_5$ alkylene;
- $Z_1$, $Z_2$, and $Z_3$ are independently selected from the group consisting of H, alkyl, aryl, and aralkyl;
- $X_3$, $X_4$, $X_5$, and $X_6$ are independently N or CH;
- $Y_1$, $Y_2$, and $Y_3$ are independently carbonyl, sulfonyl, or methylene; and
- $D_2$, $D_3$, $D_4$, and $D_5$ are independently selected from H, alkyl, halo, hydroxyl, mercapto, mercaptoalkyl, alkoxyl, aryloxyl, aralkoxyl, acyloxyl, carboxyl, alkyloxycarbonyl, aryloxycarbonyl, aralkoxycarbonyl, acylamino, carbamoyl, alkylcarbamoyl, dialkylcarbamoyl,

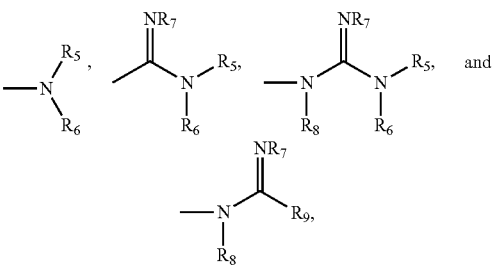

wherein $R_5$, $R_6$, $R_7$, $R_8$, and $R_9$ are independently selected from H, alkyl, aralkyl, and aryl;
or a pharmaceutically acceptable salt thereof.

In some embodiments, the compound of Formula (II) is selected from the group consisting of:

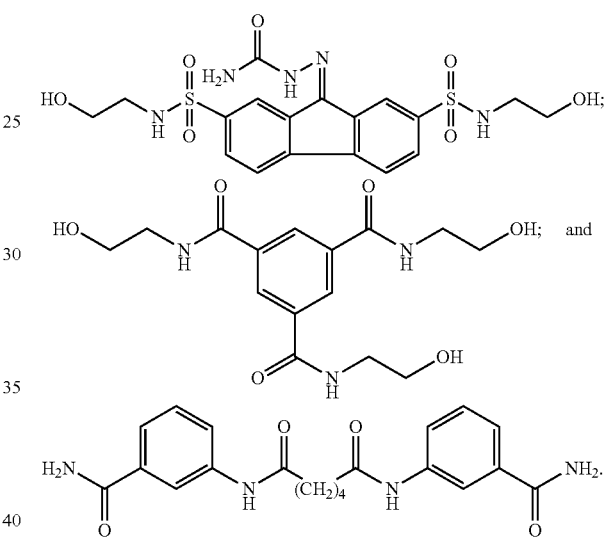

In some embodiments, the loop 2 BDNF mimetic compound has a structure of Formula (III):

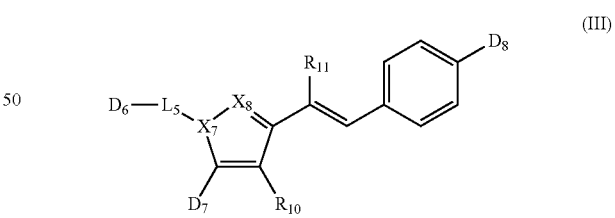

wherein:
- $L_5$ is present or absent, and when present is $C_1$-$C_5$ alkylene;
- $X_7$ and $X_8$ are independently N or CH;
- $R_{10}$ and $R_{11}$ are independently selected from the group consisting of H, halo, alkyl, and cyano;
- $D_6$, $D_7$, and $D_8$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl,

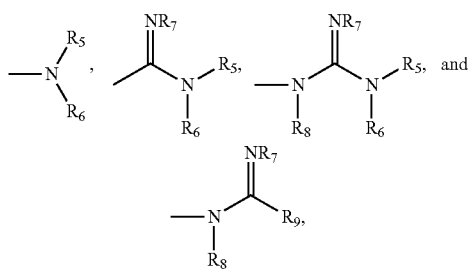

wherein $R_5$, $R_6$, $R_7$, $R_8$, and $R_9$ are independently selected from H, alkyl, aralkyl, and aryl;
or a pharmaceutically acceptable salt thereof.

In some embodiments, the compound of Formula (III) is

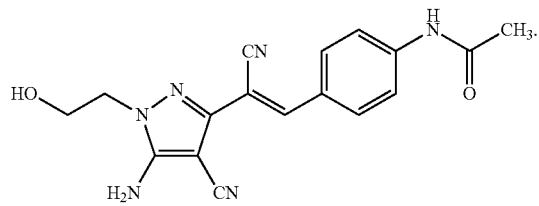 [SMILES: CC(=O)Nc1ccc(/C=C(\C#N)c2nn(CCO)c(N)c2C#N)cc1]

In some embodiments, the loop 2 BDNF mimetic has a structure of Formula (IV):

(IV)

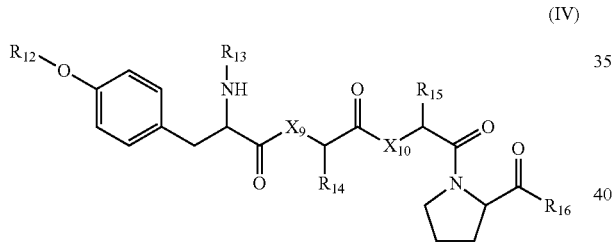

wherein:
$X_9$ and $X_{10}$ are independently $CH_2$ or $NR_4$, wherein $R_4$ is selected from H, alkyl, aralkyl and aryl;
$R_{12}$ is selected from the group consisting of H, alkyl, aralkyl, aryl, acyl, carbamoyl, alkylcarbamoyl, and dialkylcarbamoyl;
$R_{13}$ is selected from H, alkyl, aryl, aralkyl, acyl, alkoxycarbonyl, aryloxycarbonyl, aralkoxycarbonyl, carbamoyl, alkycarbamoyl, and dialkylcarbamoyl;
$R_{14}$ and $R_{15}$ are independently selected from H alkyl, substituted alkyl, and aralkyl; and
$R_{16}$ is selected from the group consisting of H, alkyl, aryl, aralkyl, hydroxyl, alkoxyl, aryloxyl, aralkoxyl, and

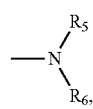

wherein $R_5$ and $R_6$ are H, alkyl, aralkyl, or aryl;
or a pharmaceutically acceptable salt thereof.

In some embodiments, the compound of Formula (IV) is

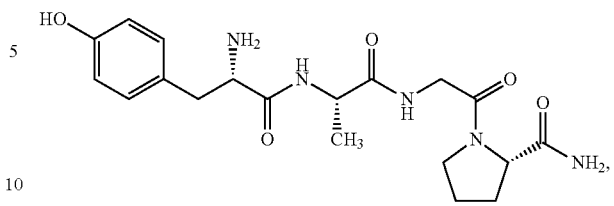

or a stereoisomer thereof.

In some embodiments, the loop 2 BDNF mimetic compound has a structure of Formula (V):

(V)

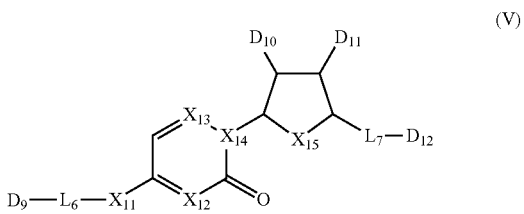

wherein:
$L_6$ and $L_7$ are independently present or absent, and if present are $C_1$-$C_5$ alkylene;
$X_{11}$ is O, S, $CH_2$ or $NR_{17}$, wherein $R_{17}$ is selected from H, alkyl, aralkyl and aryl;
$X_{12}$, $X_{13}$, and $X_{14}$ are independently CH or N;
$X_{15}$ is selected from the group consisting of O, S, and $NR_{18}$, wherein $R_{18}$ is selected from H, alkyl, aralkyl, and aryl; and
$D_9$, $D_{10}$, $D_{11}$, and $D_{12}$ are independently selected from H, alkyl, aryl, aralkyl, halo, hydroxyl, alkoxyl, aralkoxyl, aryloxyl, mercapto, mercaptoalkyl, acyloxyl, carboxyl, alkyloxycarbonyl, aryloxycarbonyl, aralkoxycarbonyl, acylamino, carbamoyl, alkylcarbamoyl, dialkylcarbamoyl,

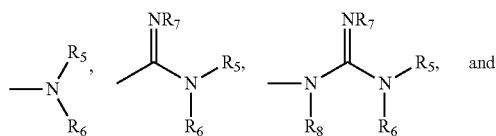

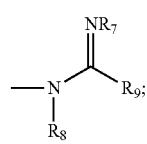

and
$R_5$, $R_6$, $R_7$, $R_8$, and $R_9$ are independently selected from H, alkyl, aralkyl, and aryl;
or a pharmaceutically acceptable salt thereof.

In some embodiments, the compound of Formula (V) is

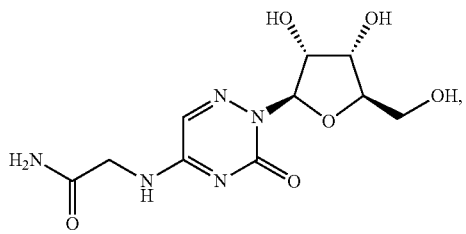 [SMILES: NC(=O)CNc1cnn([C@@H]2O[C@H](CO)[C@@H](O)[C@H]2O)c(=O)n1]

or a stereoisomer thereof.

In some embodiments, the loop 2 BDNF mimetic compound has a structure of Formula (VI):

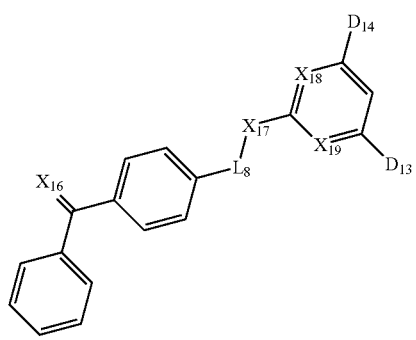

(VI)

wherein:
$L_8$ is present or absent, and when present is $C_1$-$C_5$ alkylene;
$X_{16}$ is selected from the group consisting of O, S, and $NR_{19}$, wherein $R_{19}$ is selected from H, alkyl, aralkyl and aryl;
$X_{17}$ is selected from the group consisting of O, S, $CH_2$, and $NR_{20}$, wherein $R_{20}$ is selected from H, alkyl, aralkyl, and aryl;
$X_{18}$ and $X_{19}$ are independently selected from N and CH; and
$D_{13}$ and $D_{14}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

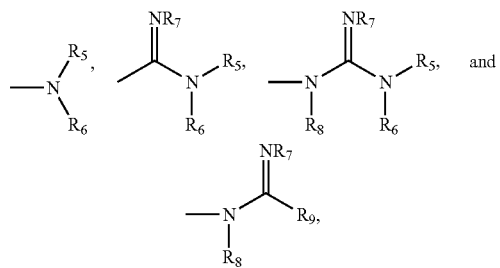

wherein $R_5$, $R_6$, $R_7$, $R_8$, and $R_9$ are independently selected from H, alkyl, aralkyl, and aryl;
or a pharmaceutically acceptable salt thereof.

In some embodiments, the compound of Formula (VI) is

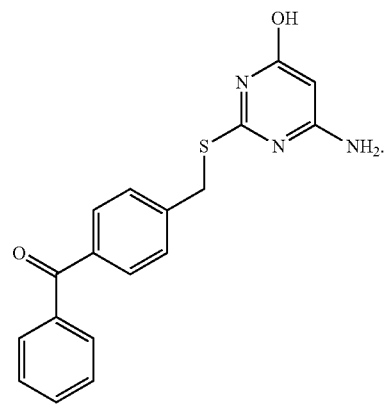 [SMILES: Nc1cc(O)nc(SCc2ccc(C(=O)c3ccccc3)cc2)n1]

In some embodiments, the loop 2 BDNF mimetic compound has a structure of Formula (VII):

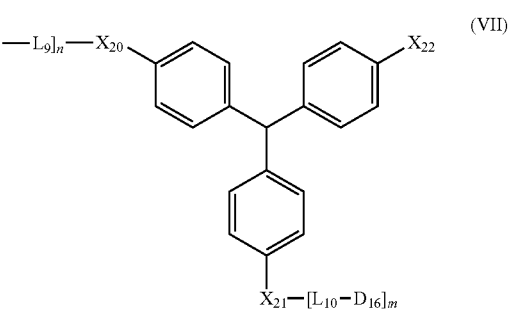

(VII)

wherein:
m and n are independently 1 or 2;
each $L_9$ and $L_{10}$ can be present or absent, and when present is $C_1$-$C_5$ alkylene;
$X_{20}$ and $X_{21}$ are independently selected from CH, $CH_2$, N, and $NR_4$, wherein $R_4$ is selected from H, alkyl, aralkyl and aryl;
$X_{22}$ is selected from H and halo; and
each $D_{15}$ and each $D_{16}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

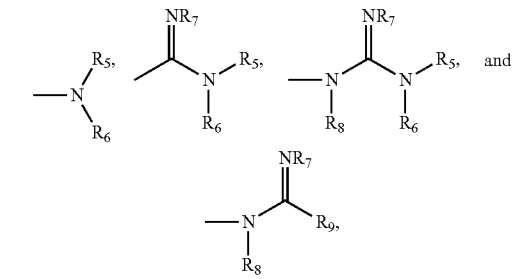

wherein $R_5$, $R_6$, $R_7$, $R_8$, and $R_9$ are independently selected from H, alkyl, aralkyl, and aryl;
or a pharmaceutically acceptable salt thereof.

In some embodiments, the compound of Formula (VII) is

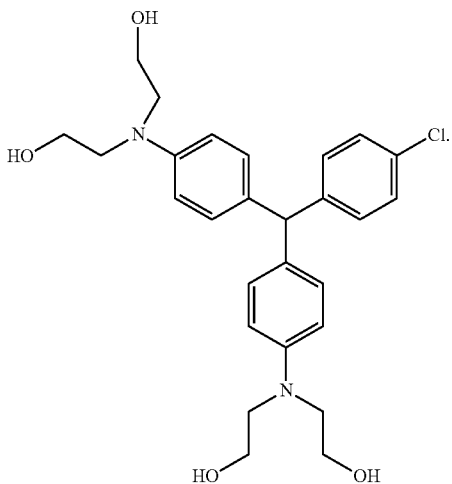 [SMILES: OCCN(CCO)c1ccc(C(c2ccc(Cl)cc2)c2ccc(N(CCO)CCO)cc2)cc1]

In some embodiments, the loop 2 BDNF mimetic compound has a structure of Formula (VIII):

(VIII)

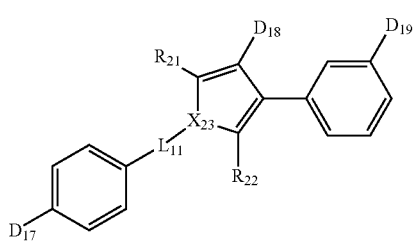

wherein:
- $L_{11}$ is present or absent, and when present is $C_1$-$C_5$ alkylene;
- $X_{23}$ is N or CH;
- $R_{21}$ and $R_{22}$ are independently selected from the group consisting of H, alkyl, aralkyl, aryl and halo; and
- $D_{17}$, $D_{18}$, and $D_{19}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

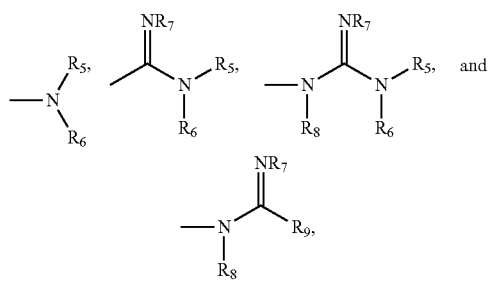

wherein $R_5$, $R_6$, $R_7$, $R_8$, and $R_9$ are independently selected from H, alkyl, aralkyl, and aryl;
or a pharmaceutically acceptable salt thereof.

In some embodiments, the compound of Formula (VIII) is selected from the group consisting of:

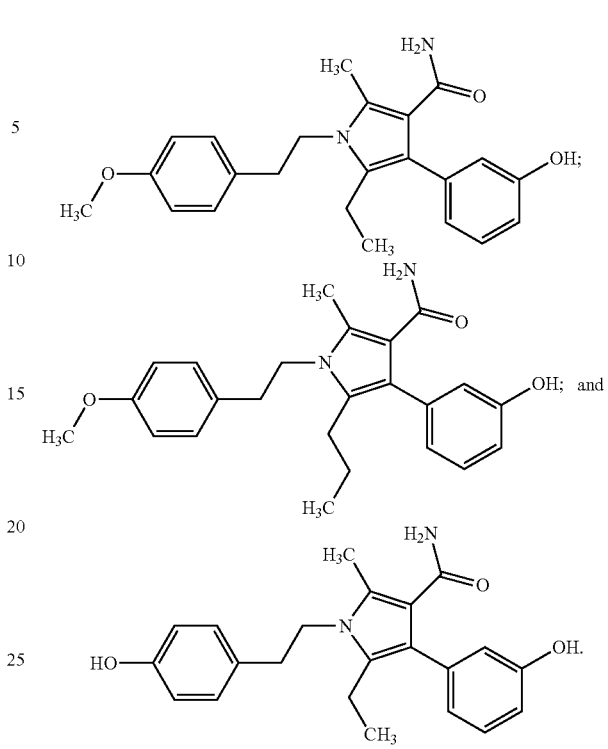

In some embodiments, the loop 2 BDNF mimetic compound has a structure of Formula (IX):

(IX)

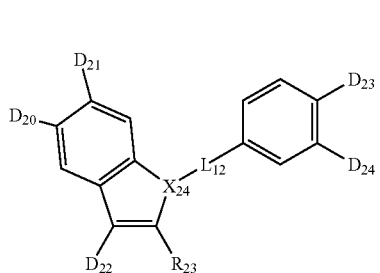

wherein:
- $L_{12}$ is present or absent, and when present is $C_1$-$C_5$ alkylene;
- $X_{24}$ is N or CH;
- $R_{23}$ is selected from the group consisting of H, alkyl, aralkyl, aryl, and halo; and
- $D_{20}$, $D_{21}$, $D_{22}$, $D_{23}$, and $D_{23}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

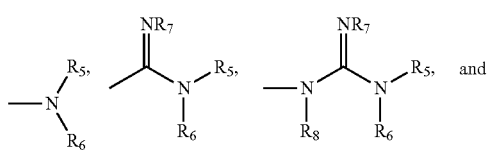

-continued

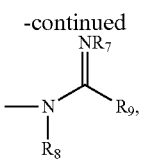

wherein $R_5$, $R_6$, $R_7$, $R_8$, and $R_9$ are independently selected from H, alkyl, aralkyl, and aryl;
or a pharmaceutically acceptable salt thereof.

In some embodiments, the compound of Formula (IX) is

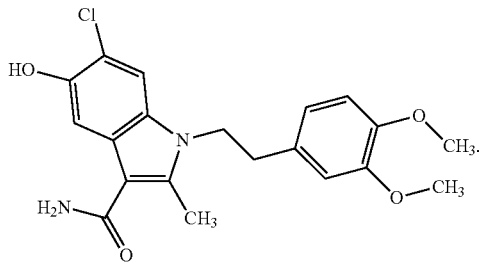 [SMILES: COc1ccc(CCn2c(C)c(C(N)=O)c3cc(O)c(Cl)cc32)cc1OC]

In some embodiments, the loop 2 BDNF mimetic compound has a structure of Formula (X):

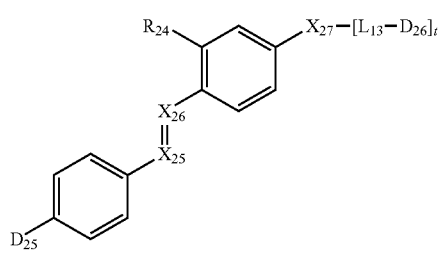

wherein:
t is 1 or 2;
each $L_{13}$ is present or absent, and when present is $C_1$-$C_5$ alkylene;
$X_{25}$ and $X_{26}$ are selected from N and CH;
$X_{27}$ is selected from N, CH, $CH_2$, and $NR_{25}$, wherein $R_{25}$ is H or alkyl;
$R_{24}$ is selected from H, alkyl, aralkyl, aryl, and halo; and
$D_{25}$ and each $D_{26}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

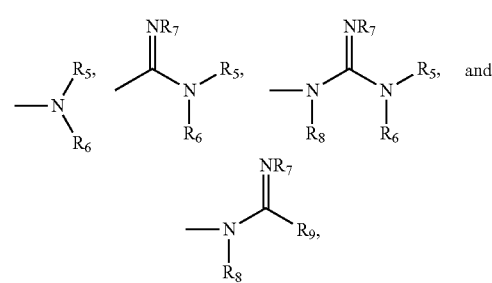

wherein $R_5$, $R_6$, $R_7$, $R_8$, and $R_9$ are independently selected from H, alkyl, aralkyl, and aryl;
or a pharmaceutically acceptable salt thereof.

In some embodiments, the compound of Formula (X) is

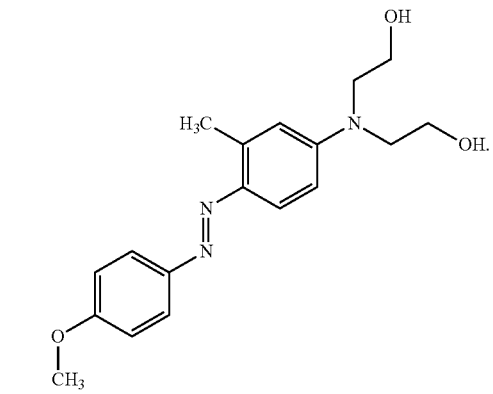 [SMILES: COc1ccc(/N=N/c2ccc(N(CCO)CCO)cc2C)cc1]

In some embodiments, the loop 2 BDNF mimetic compound has a structure of Formula (XI):

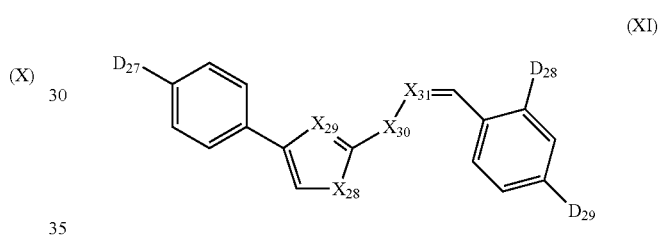

wherein:
$X_{28}$ is selected from $CH_2$, O, S, and $NR_{26}$, wherein $R_{26}$ is selected from H, alkyl, aralkyl, and aryl;
$X_{29}$ is N or CH;
$X_{30}$ is $CH_2$ or $NR_{27}$; wherein $R_{27}$ is selected from H, alkyl, aralkyl, and aryl;
$X_{31}$ is N or CH; and
$D_{27}$, $D_{28}$, and $D_{29}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

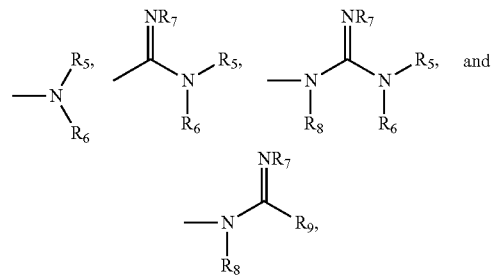

wherein $R_5$, $R_6$, $R_7$, $R_8$, and $R_9$ are independently selected from H, alkyl, aralkyl, and aryl;
or a pharmaceutically acceptable salt thereof.

In some embodiments, the compound of Formula (XI) is

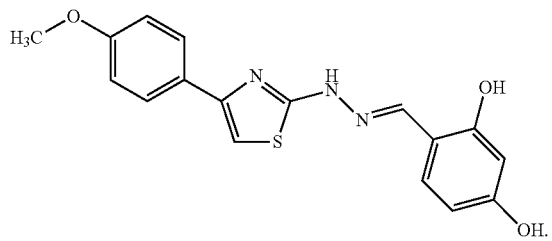 [SMILES: COc1ccc(-c2csc(N/N=C/c3ccc(O)cc3O)n2)cc1]

In some embodiments, the compound is a derivative of a parent compound having binding and/or modulation specificity for a TrkB receptor molecule, wherein the derivative also has binding and/or modulation specificity for the TrkB receptor or wherein the derivative is modified in vivo to form a compound having binding and/or modulation specificity for the TrkB receptor. In some embodiments, the derivative exhibits an enhancement in at least one of the characteristics selected from the group consisting of potency, selectivity, hydrophilicity, lipophilicity, amphipathicity, solubility, bioavailability, and resistance to hepatic degradation, as compared to the parent compound.

An object of the presently disclosed subject matter is to provide methods of and compositions for facilitating neural cell survival or promoting the function of neurons or other TrkB-bearing cells using BDNF small molecule mimetics.

An object of the presently disclosed subject matter having been stated hereinabove, and which is addressed in whole or in part by the present presently disclosed subject matter, other objects will become evident as the description proceeds when taken in connection with the accompanying examples and drawings as best described hereinbelow.

DETAILED DESCRIPTION

Figure 1:
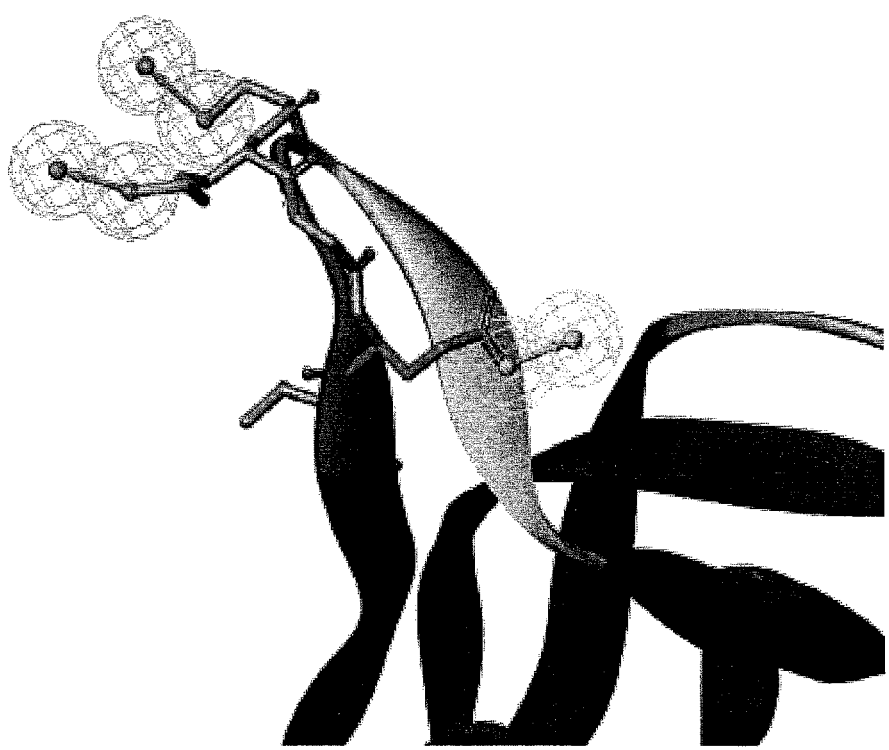
FIG. 1 is a ribbon representation of the X-ray crystal structure of a portion of human BDNF peptide including loop 2. Hydrogen bonding features are represented by pairs of spheres with their relative positions indicating the locations of the acceptor and donor. One of the spheres of each pair is centered on putative acceptor/donor features in the model, while the other (i.e., the sphere centered on the pointed end of the arrow) indicates the target location of a complementary feature on any potentially interacting molecule. The diameter of the spheres represents a spatial tolerance for chemical feature matching in 3D conformer library scans.

In subjects with particular disorders, including neurological and other disorders, alterations in neurotrophin localization, expression levels of neurotrophins, and/or expression levels of the receptors that bind neurotrophins can occur. Accordingly, by providing subjects suffering from such disorders with a corresponding neurotrophic factor or mimetic thereof, such neural degeneration can be alleviated or prevented. In some cases, inhibition of neurotrophin function would be of benefit. As disclosed for the first time herein, methods of treating a disorder and/or facilitating neural cell survival by administering a non-peptide compound having binding and/or modulation specificity for the TrkB receptor molecule are provided.

The methods and compounds of the presently disclosed subject matter relate to compounds having binding and/or modulation specificity for the TrkB receptor molecule. As used herein, discovery by in silico screening of compounds having binding and/or modulation specificity for the TrkB receptor are suitable for positively regulating survival or function of neural and other cells. Particularly, in cells showing trophic responses to neurotrophins, the compounds can promote survival signaling.

I. Definitions

It is to be understood that the terminology used herein is for the purpose of describing particular embodiments only and is not intended to be limiting. Throughout the specification and claims, a given chemical formula or name shall encompass all optical and stereoisomers, as well as racemic mixtures where such isomers and mixtures exist.

Unless defined otherwise, all technical and scientific terms used herein have the same meaning as commonly understood to one of ordinary skill in the art to which the presently disclosed subject matter belongs. Although any methods and materials similar or equivalent to those described herein can be used in the practice or testing of the presently disclosed subject matter, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, time, dose, etc. is meant to encompass in one example variations of ±20% or ±10%, in another example ±5%, in another example ±1%, and in yet another example ±0.1% from the specified amount, as such variations are appropriate to perform the disclosed methods.

As used herein, the term "neurological disorder" includes any disorder characterized by damage of nervous system cells and include the following, without limitation, Alzheimer's disease, Huntington's disease, amyotrophic lateral sclerosis (ALS), epilepsy, Parkinson's disease, spinal cord injury, stroke, hypoxia, ischemia, brain injury, diabetic neuropathy, peripheral neuropathy, nerve transplantation complications, multiple sclerosis, peripheral nerve injury, and conditions involving degeneration or dysfunction of cells expressing Trkb.

As used herein the term "alkyl" refers to $C_{1-20}$ inclusive, linear (i.e., "straight-chain"), branched, or cyclic (a "cycloalkyl"), saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Further, as used herein, the terms alkyl and/or "substituted alkyl" include an "allyl" or an "allylic group." The terms "allylic group" or "allyl" refer to the group —CH$_2$HC=CH$_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, fluorene, and the like.

A structure represented generally by a formula such as:

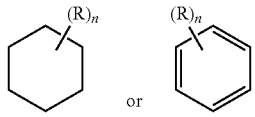

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

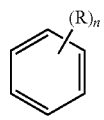

wherein n is an integer from 0 to 2 comprises compound groups including, but not limited to:

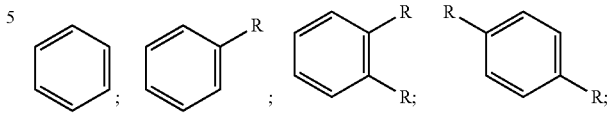

and the like.

The structure:

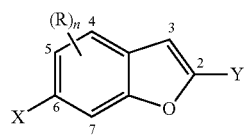

wherein n is one (1) comprises compound groups including:

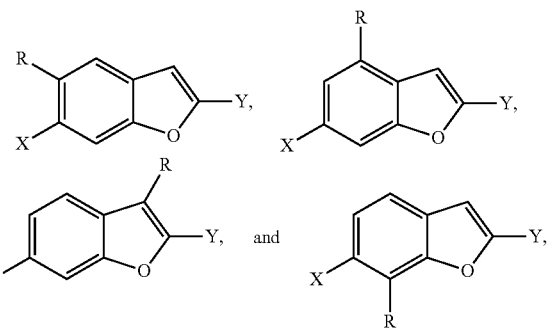

wherein the one (1) R substituent can be attached at any carbon on the benzofuran parent structure not occupied by another designated substituent, as in this case carbon 6 is substituted by X and carbon 2 is substituted by Y.

A dashed line representing a bond in a cyclic ring structure indicates that the bond can be either present or absent in the ring. That is a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)$_3$—); cyclohexylene (—$C_6H_{10}$—); —CH=CH—CH=CH—; —CH=CH—

CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e.,

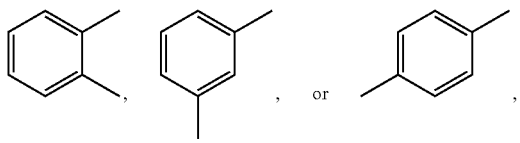

respectively. The arylene group can also be napthylene or a divalent fluorene moiety. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-)

As used herein, the term "acyl" refers to an organic acid group wherein the —OH of the carboxyl group has been replaced with another substituent (i.e., as represented by RCO—, wherein R is an alkyl, aralkyl, or aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include, but are not limited to, cyclopropyl, cyclobutyl, cyclopentyl, cyclohexyl, cycloheptyl, and the like. Further, the cycloalkyl group can be optionally substituted with a linking group, such as an alkylene group as defined hereinabove, for example, methylene, ethylene, propylene, and the like. In such cases, the cycloalkyl group can be referred to as, for example, cyclopropylmethyl, cyclobutylmethyl, and the like. Additionally, multicyclic cycloalkyl rings include adamantyl, octahydronaphthyl, decalin, camphor, camphane, and noradamantyl.

"Alkoxyl" or "alkoxy" refer to an alkyl-O— group wherein alkyl is as previously described. The term "alkoxyl" as used herein can refer to C$_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

The term "aralkoxyl" refers to an aralkyl-O group wherein aralkyl is as described above.

"Aralkyloxyl" refers to an aralkyl-O— group wherein the aralkyl group is as previously described. An exemplary aralkyloxyl group is benzyloxyl.

"Alkylamino" refers to an —NHR group wherein R is an alkyl group or substituted alkyl group as previously described.

"Dialkylamino" refers to an —NRR' group wherein each of R and R' is independently an alkyl group and/or a substituted alkyl group as previously described. Exemplary dialkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an H$_2$N—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

The term "alkenylene" denotes an acyclic carbon chain (i.e., having an open-chain structure) having a carbon-to-carbon double bond and is represented by the formula C$_n$H$_{2n-2}$, which optionally can be substituted one or more times. Representative alkenylene groups include, but are not limited to, ethenylene, propenylene, 1- or 2-butenylene, 1-, or 2-pentylene, and the like.

"Aroylamino" refers to an aroyl-NH— group wherein aroyl is as previously described.

The term "amino" refers to the —NH$_2$ group.

The term "carbonyl" refers to the —(C=O)— group.

The term "carboxyl" refers to the —COOH group.

The term "cyano" refers to the —CN group.

The terms "halo", "halide", or "halogen" as used herein refer to fluoro, chloro, bromo, and iodo groups.

The terms "hydroxyl" and "hydroxy" refer to the —OH group.

The term "hydroxyalkyl" refers to an alkyl group substituted with an —OH group.

The term "mercapto" refers to the —SH group.

The term "mercaptoalkyl refers to the —SR group wherein R is alkyl or substituted alkyl.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term "sulfonyl" refers to the —$S(=O)_2$— group.

The term "cycloalkenyl" refers to a partially unsaturated cyclic hydrocarbon group containing one or more rings, for example, one ring, two rings, three rings, or four rings, with three or more carbon atoms per ring, for example, 3, 4, 5, 6, 7, or 8 carbon atoms per ring. Exemplary cycloalkenyl groups include, but are not limited to, cyclopropenyl, cyclobutenyl, cyclopentenyl, cyclohexenyl, and the like.

The term "substituted cycloalkenyl" refers to a cycloalkenyl group substituted with one or more substituents, preferably 1, 2, 3, or 4 substituents, at any available point of attachment. Exemplary substituents include, but are not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

A named "R," "X," "Y," "D," "L," or "Z" group will generally have the structure that is recognized in the art as corresponding to a group having that name, unless specified otherwise herein. For the purposes of illustration, certain representative "R," "X," "Y," "D," "L," and "Z" groups as set forth above are defined below. These definitions are intended to supplement and illustrate, not preclude, the definitions that would be apparent to one of ordinary skill in the art upon review of the present disclosure.

The term "treatment" as used herein covers any treatment of a disease, disorder, and/or condition in an animal or mammal, particularly a human, and includes: (i) preventing a disease, disorder and/or condition from occurring in a person which can be predisposed to the disease, disorder and/or condition, or at risk for being exposed to an agent that can cause the disease, disorder, and/or condition; but, has not yet been diagnosed as having it; (ii) inhibiting the disease, disorder and/or condition, i.e., arresting its development; and (iii) relieving the disease, disorder and/or condition, i.e., causing regression of the disease, disorder and/or condition.

The term "mimetic" refers to a compound having similar functional and/or structural properties to another known compound or a particular fragment of that known compound, such as a known compound of biological origin, e.g., a polypeptide or fragment thereof.

"Binding specificity" refers to the ability of a protein or other type of molecule capable of recognizing and interacting with a complementary site on another protein or other type of molecule. As used herein, the term binding specificity can refer to the ability of a molecule to bind preferentially to one type of molecule over another. For example, binding specificity can refer the ability of a BDNF mimetic to preferentially bind to TrkB as opposed to TrkA or TrkC. A molecule having binding specificity for a receptor can be used for one or more of contacting the receptor, activating the receptor, and inhibiting the receptor.

The term "modulation specificity" as used herein refers to a molecule that can modulate the activity of one receptor preferentially. The molecule can modulate the activity of one receptor to a greater extent than another receptor or can modulate the activity of one receptor in a group of receptors exclusively. For example, a BDNF mimetic can specifically modulate the activity of TrkB and not TrkA or TrkC. The modulation of activity can include, but is not limited to, upregulation, downregulation, activation, partial activation, agonism, partial agonism, antagonism, partial antagonism, inhibition, partial inhibition, or a combination thereof. A molecule having modulation specificity for a receptor can be used, for example, to contact and activate a receptor or to contact and inhibit a receptor.

The term "binding and/or modulation specificity" refers to a molecule that can bind a designated receptor, modulate the activity of a designated receptor, or both bind and modulate the activity of a designated receptor.

The term "pharmacophore", as used herein, refers to a molecular moiety capable of exerting a selected biochemical effect, e.g., inhibition of an enzyme, binding to a receptor, chelation of an ion, and the like. A selected pharmacophore can have more than one biochemical effect, e.g., can be an inhibitor of one enzyme and an agonist of a second enzyme. A therapeutic agent can include one or more pharmacophores, which can have the same or different biochemical activities.

The term "derivative" as used herein refers to a compound chemically modified so as to differentiate it from a parent compound. Such chemical modifications can include, for example, replacement of hydrogen by an alkyl, acyl, or amino group. A derivative compound can be modified by, for example, glycosylation, pegylation, or any similar process that retains at least one biological or immunological function of the compound from which it was derived.

The terms "small molecule" and "small peptide" refer to compounds having molecular weights below 1000. In some embodiments, the small molecule or small peptide is a compound having a molecular weight below 750. In some embodiments, the small molecule or small peptide has a molecular weight below 500.

The term "peptide" refers to any polymer comprising amino acids linked by amide bonds between the amino group of each amino acid and the carboxyl group of the neighboring amino acid. Each amino acid unit making up the peptide is referred to as a "residue." Thus the term "amino acid residue" refers to the radical or diradical of one of the 20 standard amino acids or of a nonstandard amino acid that results from the loss of a proton from the amine group, the loss of the hydroxyl from the carboxylic acid group, or the loss of both a proton from the amine group and the hydroxyl from the carboxylic acid group. The term "peptide" also refers to derivatives of peptides wherein the amino terminus, the carboxyl terminus, one or more amino acid side chain, or a combination thereof has been chemically modified or derivatized, for example, through acylation, alkylation, reduction, or amidation, or any other method known in the art of peptide chemistry.

The term "stereoisomer" as it relates to a given compound is well understood in the art, and refers to another compound having the same molecular formula, wherein the atoms making up the other compound differ in the way they are oriented in space, but wherein the atoms in the other compound are like the atoms in the given compound with respect to which atoms are joined to which other atoms (e.g., an enantiomer, a diastereomer, or a geometric isomer).

The term "hydrophilicity" is used in the common manner of the field as having an affinity for water; readily absorbing and/or dissolving in water.

The term "lipophilicity" is used in the common manner of the field as having an affinity for, tending to combine with, or capable of dissolving in lipids.

The term "amphipathicity", as used herein, describes a structure having discrete hydrophobic and hydrophilic regions. Thus, one portion of the structure interacts favorably with aqueous and other polar media, while another portion of the structure interacts favorably with non-polar media.

The term "solubility" as used herein, describes the maximum amount of solute that will dissolve in a given amount of solvent at a specified temperature.

The term "bioavailability" as used herein refers to the systemic availability (i.e., blood/plasma levels) of a given amount of compound administered to a subject. The term further encompasses the rate and extent of absorption of compound that reaches the site of action.

II. Compounds

The presently disclosed subject matter provides compounds having binding and/or modulation specificity for the TrkB receptor molecule. In some embodiments, the compounds are mimetics of a neurotrophin β-turn loop. In some embodiments, the neurotrophin is BDNF. In some embodiments, the β-turn loop is loop 2 of BDNF. These compounds can be used in accordance with the presently disclosed pharmaceutical compounds and methods in the treatment and prevention of disorders, including but not limited to neurological disorders (e.g., neurodegenerative disorders).

Some TrkB binding and/or modulation compounds demonstrate agonist function and thus promote TrkB activation. Some TrkB binding and/or modulation compounds demonstrate partial agonist function. These compounds can be used to promote TrkB function or in some cases to partially block the function of endogenous BDNF. Inhibition of BDNF function can prove useful for prevention or treatment of epilepsy or other disorders in which excessive BDNF function contributes to underlying disease mechanisms. Some TrkB binding and/or modulation compounds demonstrate no agonist activity and thus might prove useful as TrkB antagonists.

The TrkB binding and/or modulation compounds of the presently disclosed subject matter can be isolated from natural sources, purchased from commercial sources, or synthesized or partially synthesized by methodology known in the art of synthetic organic chemistry, including parallel and combinatorial synthetic techniques.

II.A. Structure

In accordance with the presently disclosed subject matter, a representative compound or mimetic of BDNF β-turn loop 2 having binding and/or modulation specificity for a TrkB receptor molecule can comprise a compound having a structure of one of Formulas (I-XI).

In some embodiments, the loop 2 BDNF mimetic compound has a structure of Formula (I):

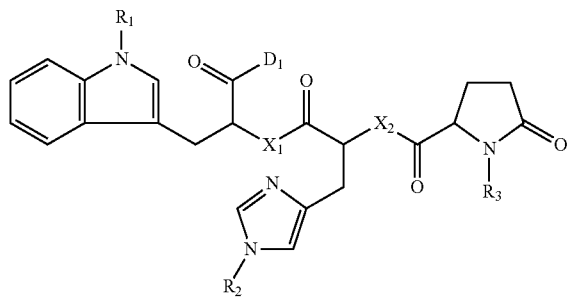

wherein:
$R_1$, $R_2$, and $R_3$ are independently selected from the group consisting of H, alkyl, aryl, aralkyl, acyl, alkoxycarbonyl, aryloxycarbonyl, aralkoxycarbonyl, carbamoyl, alkylcarbamoyl, and dialkylcarbamoyl;

$X_1$ and $X_2$ are independently selected from $CH_2$ and $NR_4$, wherein $R_4$ is selected from H, alkyl, aralkyl, and aryl; and $D_1$ is selected from the group consisting of H, alkyl, aryl, aralkyl, hydroxyl, alkoxyl, aryloxyl, aralkoxyl, and

wherein $R_5$ and $R_6$ are H, alkyl, aralkyl, or aryl; or a pharmaceutically acceptable salt.

In some embodiments, $R_1$, $R_2$, and $R_3$ are H, $X_1$ and $X_2$ are NH, and $D_1$ is alkoxy. In some embodiments, the compound of Formula (I) is

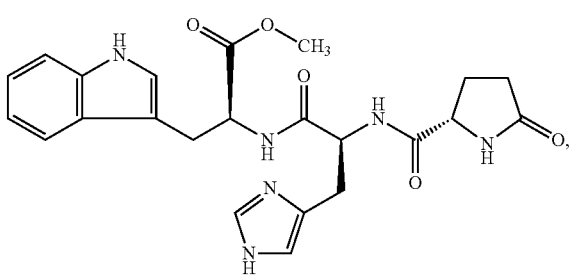 [SMILES: COC(=O)[C@H](Cc1c[nH]c2ccccc12)NC(=O)[C@H](Cc1c[nH]cn1)NC(=O)[C@@H]1CCC(=O)N1]

or a stereoisomer thereof.

In some embodiments, the loop 2 BDNF mimetic compound has a structure of Formula (II):

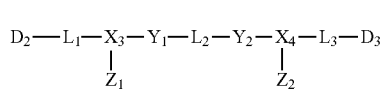

wherein:
$L_1$ and $L_3$ are independently selected from the group consisting of $C_1$-$C_5$ alkylene, arylene, aralkylene, and substituted arylene;

$L_2$ is selected from the group consisting of $C_1$-$C_5$ alkylene, arylene, aralkylene, substituted arylene,

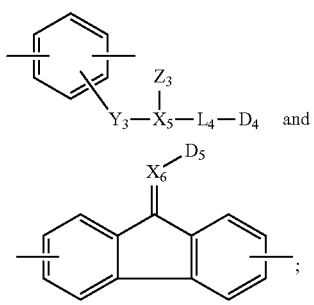

L₄ is $C_1$-$C_5$ alkylene;

$Z_1$, $Z_2$, and $Z_3$ are independently selected from the group consisting of H, alkyl, aryl, and aralkyl;

$X_3$, $X_4$, $X_5$, and $X_6$ are independently N or CH;

$Y_1$, $Y_2$, and $Y_3$ are independently carbonyl, sulfonyl, or methylene; and $D_2$, $D_3$, $D_4$, and $D_5$ are independently selected from H, alkyl, halo, hydroxyl, mercapto, mercaptoalkyl, alkoxyl, aryloxyl, aralkoxyl, acyloxyl, carboxyl, alkyloxycarbonyl, aryloxycarbonyl, aralkoxycarbonyl, acylamino, carbamoyl, alkylcarbamoyl, dialkylcarbamoyl,

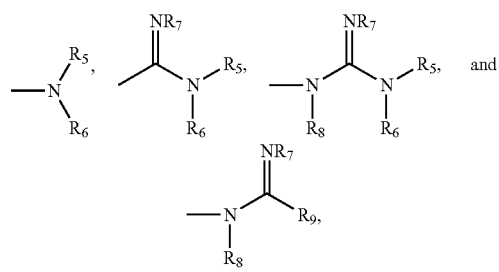

wherein $R_5$, $R_6$, $R_7$, $R_8$, and $R_9$ are independently selected from H, alkyl, aralkyl, and aryl;

or a pharmaceutically acceptable salt thereof.

In some embodiments, $L_1$ and $L_3$ are $C_1$-$C_5$ alkylene or phenylene. In some embodiments, $D_2$ and $D_3$ are hydroxyl or carbamoyl. In some embodiments, $X_3$ and $X_4$ are N. In some embodiments, the compound of Formula (II) is selected from the group consisting of:

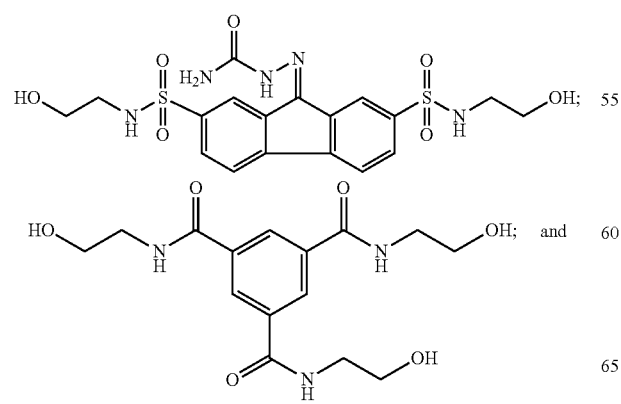

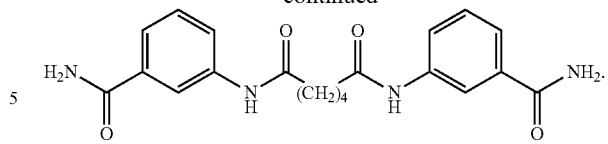

In some embodiments, the loop 2 BDNF mimetic compound has a structure of Formula (III):

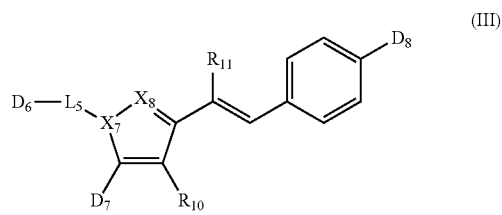

wherein:

$L_5$ is present of absent, and when present is $C_1$-$C_5$ alkylene;

$X_7$ and $X_8$ are independently N or CH;

$R_{10}$ and $R_{11}$ are independently selected from the group consisting of H, halo, alkyl, and cyano;

$D_6$, $D_7$, and $D_8$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl,

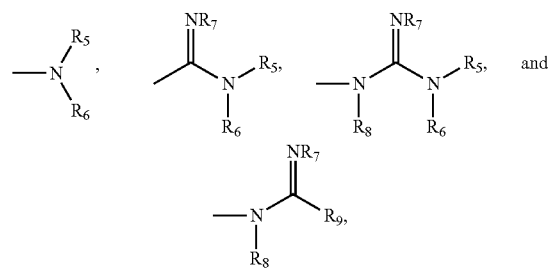

wherein $R_5$, $R_6$, $R_7$, $R_8$, and $R_9$ are independently selected from H, alkyl, aralkyl, and aryl;

or a pharmaceutically acceptable salt thereof.

In some embodiments, $R_{10}$ and $R_{11}$ are cyano. In some embodiments, $D_6$ is hydroxyl. In some embodiments, $D_7$ is $NR_5R_6$. In some embodiments, $D_8$ is acylamino. In some embodiments, the compound of Formula (III) is

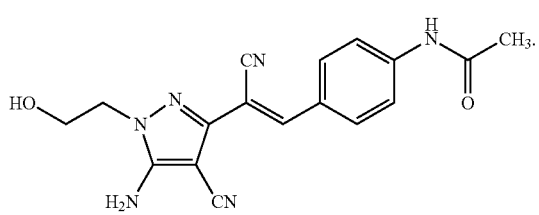

In some embodiments, the loop 2 BDNF mimetic has a structure of Formula (IV):

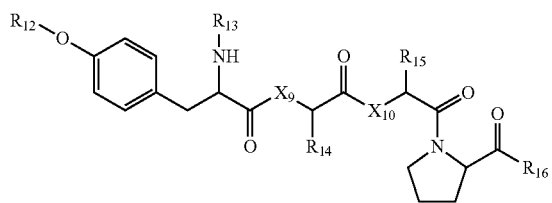

(IV)

wherein:

$X_9$ and $X_{10}$ are independently $CH_2$ or $NR_4$, wherein $R_4$ is selected from H, alkyl, aralkyl and aryl;

$R_{12}$ is selected from the group consisting of H, alkyl, aralkyl, aryl, acyl, carbamoyl, alkylcarbamoyl, and dialkylcarbamoyl;

$R_{13}$ is selected from H, alkyl, aryl, aralkyl, acyl, alkoxycarbonyl, aryloxycarbonyl, aralkoxycarbonyl, carbamoyl, alkycarbamoyl, and dialkylcarbamoyl;

$R_{14}$ and $R_{15}$ are independently selected from H alkyl, substituted alkyl, and aralkyl; and $R_{16}$ is selected from the group consisting of H, alkyl, aryl, aralkyl, hydroxyl, alkoxyl, aryloxyl, aralkoxyl, and

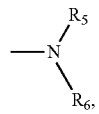

wherein $R_5$ and $R_6$ are H, alkyl, aralkyl, or aryl;

or a pharmaceutically acceptable salt thereof.

In some embodiments, $R_{12}$, $R_{13}$, $R_{14}$, and $R_{15}$ are H or alkyl. In some embodiments, $X_9$ and $X_{10}$ are $NR_4$. In some embodiments, $R_{16}$ is $NR_5R_6$, wherein $R_5$ and $R_6$ are H or alkyl. In some embodiments, the compound of Formula (IV) is

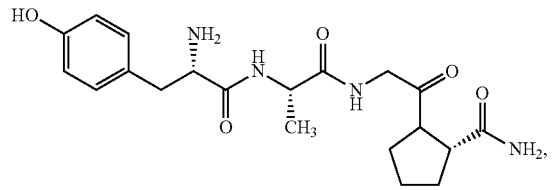 [SMILES: C[C@H](NC(=O)[C@@H](N)Cc1ccc(O)cc1)C(=O)NCC(=O)C1CCC[C@H]1C(N)=O]

or a stereoisomer thereof.

In some embodiments, the loop 2 BDNF mimetic compound has a structure of Formula (V):

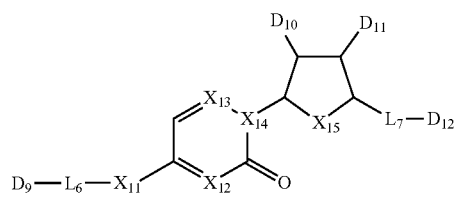

(V)

wherein:

$L_6$ and $L_7$ are independently present or absent, and when present are $C_1$-$C_5$ alkylene;

$X_{11}$ is O, S, $CH_2$ or $NR_{17}$, wherein $R_{17}$ is selected from H, alkyl, aralkyl and aryl;

$X_{12}$, $X_{13}$, and $X_{14}$ are independently CH or N;

$X_{15}$ is selected from the group consisting of O, S, and $NR_{18}$, wherein $R_{18}$ is selected from H, alkyl, aralkyl, and aryl; and $D_9$, $D_{10}$, $D_{11}$, and $D_{12}$ are independently selected from H, alkyl, aryl, aralkyl, halo, hydroxyl, alkoxyl, aralkoxyl, aryloxyl, mercapto, mercaptoalkyl, acyloxyl, carboxyl, alkyloxycarbonyl, aryloxycarbonyl, aralkoxycarbonyl, acylamino, carbamoyl, alkylcarbamoyl, dialkylcarbamoyl,

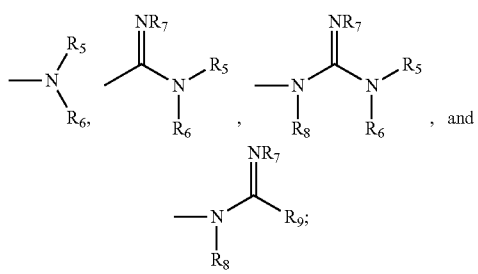

and $R_5$, $R_6$, $R_7$, $R_8$, and $R_9$ are independently selected from H, alkyl, aralkyl, and aryl;

or a pharmaceutically acceptable salt thereof.

In some embodiments, $D_9$, $D_{10}$, $D_{11}$, and $D_{12}$ are hydroxyl, alkoxyl or carbamoyl. In some embodiments, the compound of Formula (V) is

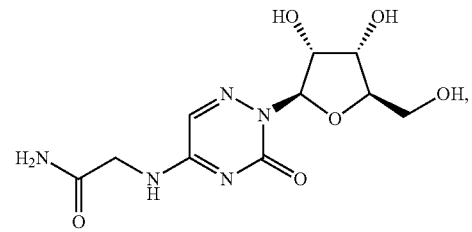 [SMILES: NC(=O)CNc1cnn([C@@H]2O[C@H](CO)[C@@H](O)[C@H]2O)c(=O)n1]

or a stereoisomer thereof.

In some embodiments, the loop 2 BDNF mimetic compound has a structure of Formula (VI):

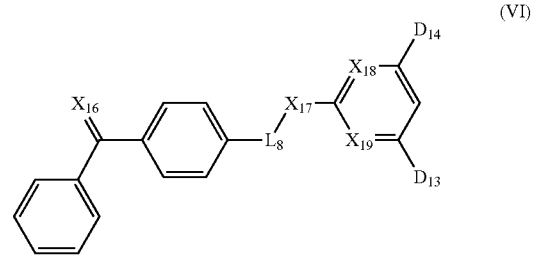

(VI)

wherein:

$L_8$ is present or absent, and when present is $C_1$-$C_5$ alkylene;

$X_{16}$ is selected from the group consisting of O, S, and $NR_{19}$, wherein $R_{19}$ is selected from H, alkyl, aralkyl and aryl;

$X_{17}$ is selected from the group consisting of O, S, $CH_2$, and $NR_{20}$, wherein $R_{20}$ is selected from H, alkyl, aralkyl, and aryl;

$X_{18}$ and $X_{19}$ are independently selected from N and CH; and $D_{13}$ and $D_{14}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

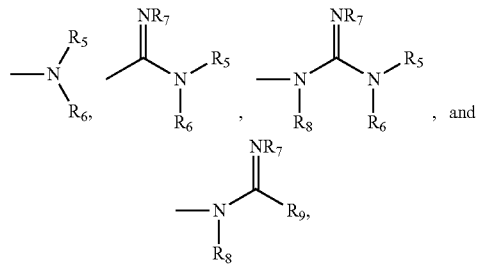

wherein $R_5$, $R_6$, $R_7$, $R_8$, and $R_9$ are independently selected from H, alkyl, aralkyl, and aryl;

or a pharmaceutically acceptable salt thereof.

In some embodiments, $D_{13}$ and $D_{14}$ are hydroxyl, alkoxyl, or $NR_5R_6$, wherein $R_5$ and $R_6$ are H or alkyl. In some embodiments, the compound of Formula (VI) is

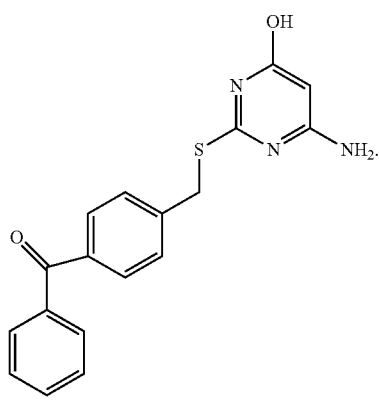 [SMILES: Nc1cc(O)nc(SCc2ccc(C(=O)c3ccccc3)cc2)n1]

In some embodiments, the loop 2 BDNF mimetic compound has a structure of Formula (VII):

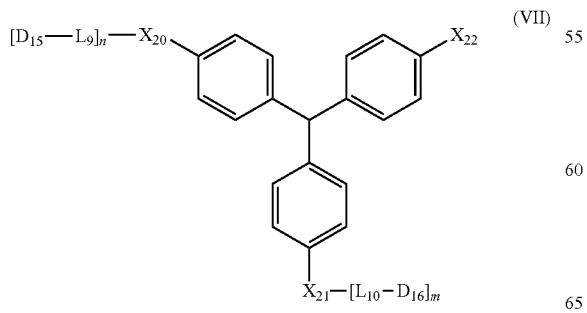

(VII)

wherein:

m and n are independently 1 or 2;

each $L_9$ and $L_{10}$ can be present or absent, and when present is $C_1$-$C_5$ alkylene;

$X_{20}$ and $X_{21}$ are independently selected from CH, $CH_2$, N, and $NR_4$, wherein $R_4$ is selected from H, alkyl, aralkyl and aryl;

$X_{22}$ is selected from H and halo; and each $D_{15}$ and each $D_{16}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

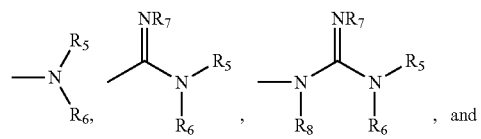

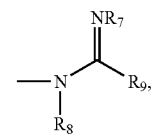

wherein $R_5$, $R_6$, $R_7$, $R_8$, and $R_9$ are independently selected from H, alkyl, aralkyl, and aryl;

or a pharmaceutically acceptable salt thereof.

In some embodiments, $X_{22}$ is halo. In some embodiments, each $D_{15}$ and each $D_{16}$ are hydroxyl. In some embodiments, the compound of Formula (VII) is

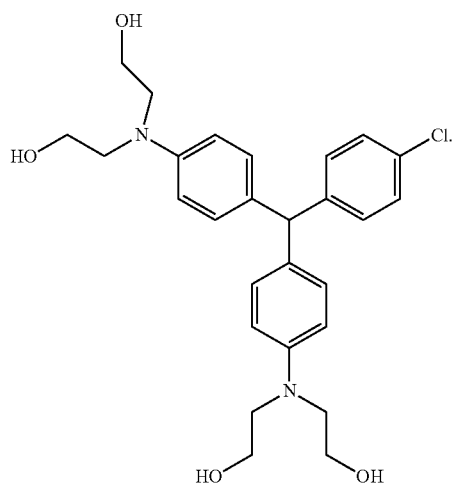 [SMILES: OCCN(CCO)c1ccc(C(c2ccc(Cl)cc2)c2ccc(N(CCO)CCO)cc2)cc1]

In some embodiments, the loop 2 BDNF mimetic compound has a structure of Formula (VIII):

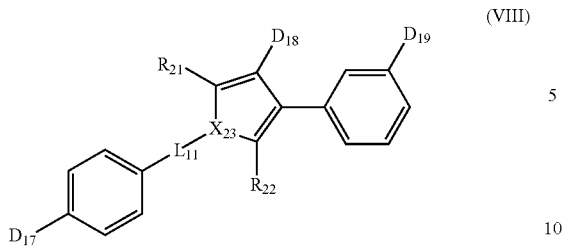

(VIII)

wherein:

$L_{11}$ is present or absent, and when present is $C_1$-$C_5$ alkylene;

$X_{23}$ is N or CH;

$R_{21}$ and $R_{22}$ are independently selected from the group consisting of H, alkyl, aralkyl, aryl and halo; and $D_{17}$, $D_{18}$, and $D_{19}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

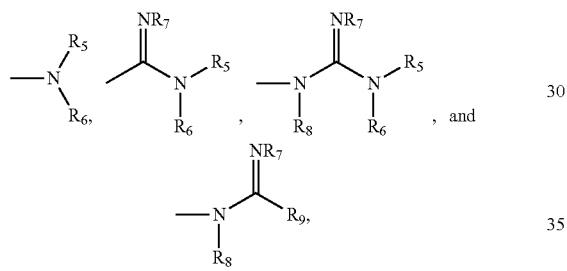

wherein $R_5$, $R_6$, $R_7$, $R_8$, and $R_9$ are independently selected from H, alkyl, aralkyl, and aryl;

or a pharmaceutically acceptable salt thereof.

In some embodiments, $R_{21}$ and $R_{22}$ are alkyl. In some embodiments, $D_{17}$, $D_{18}$, and $D_{19}$ are selected from hydroxyl, alkoxyl, and carbamoyl. In some embodiments, the compound of Formula (VIII) is selected from the group consisting of:

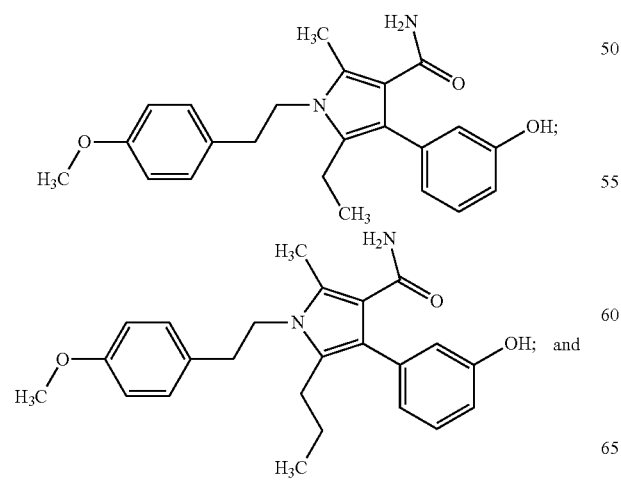

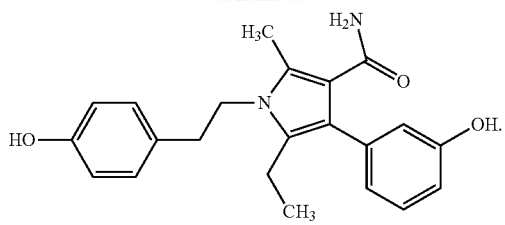

In some embodiments, the loop 2 BDNF mimetic compound has a structure of Formula (IX):

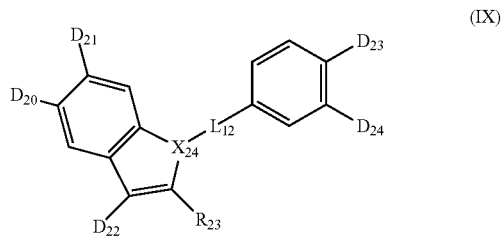

(IX)

wherein:

$L_{12}$ is present or absent, and when present is $C_1$-$C_5$ alkylene;

$X_{24}$ is N or CH;

$R_{23}$ is selected from the group consisting of H, alkyl, aralkyl, aryl, and halo; and $D_{20}$, $D_{21}$, $D_{22}$, $D_{23}$, and $D_{24}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

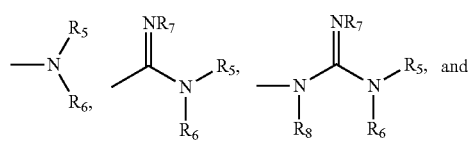

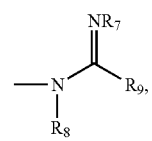

wherein $R_5$, $R_6$, $R_7$, $R_8$, and $R_9$ are independently selected from H, alkyl, aralkyl, and aryl;

or a pharmaceutically acceptable salt thereof.

In some embodiments, $D_{20}$, $D_{21}$, $D_{22}$, $D_{23}$, and $D_{24}$ are selected from hydroxyl, alkoxyl, halo, and carbamoyl. In some embodiments, $R_{23}$ is alkyl. In some embodiments, the compound of Formula (IX) is

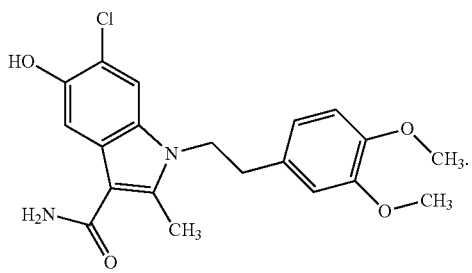 [SMILES: COc1ccc(CCn2c(C)c(C(N)=O)c3cc(O)c(Cl)cc32)cc1OC]

In some embodiments, the loop 2 BDNF mimetic compound has a structure of Formula (X):

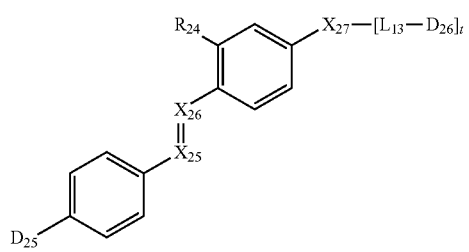

wherein:

t is 1 or 2;

each $L_{13}$ is present or absent, and when present is $C_1$-$C_5$ alkylene;

$X_{25}$ and $X_{26}$ are selected from N and CH;

$X_{27}$ is selected from N, CH, $CH_2$, and $NR_{25}$, wherein $R_{25}$ is H or alkyl;

$R_{24}$ is selected from H, alkyl, aralkyl, aryl, and halo; and $D_{25}$ and each $D_{26}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

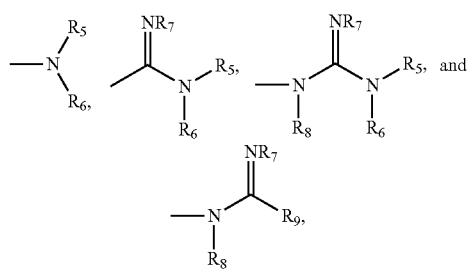

wherein $R_5$, $R_6$, $R_7$, $R_8$, and $R_9$ are independently selected from H, alkyl, aralkyl, and aryl;

or a pharmaceutically acceptable salt thereof.

In some embodiments, $D_{25}$ and each $D_{26}$ are selected from hydroxyl and alkoxyl. In some embodiments, $R_{24}$ is alkyl. In some embodiments, the compound of Formula (X) is

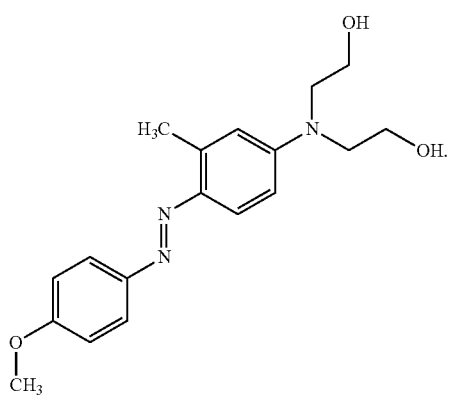

In some embodiments, the loop 2 BDNF mimetic compound has a structure of Formula (XI):

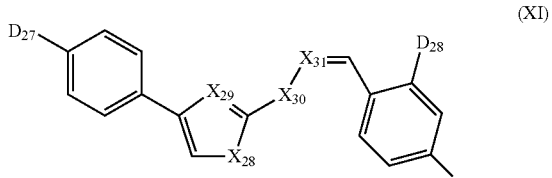

wherein:

$X_{28}$ is selected from $CH_2$, O, S, and $NR_{26}$, wherein $R_{26}$ is selected from H, alkyl, aralkyl, and aryl;

$X_{29}$ is N or CH;

$X_{30}$ is $CH_2$ or $NR_{27}$; wherein $R_{27}$ is selected from H, alkyl, aralkyl, and aryl;

$X_{31}$ is N or CH; and $D_{27}$, $D_{28}$, and $D_{29}$ are independently selected from H, alkyl, aryl, aralkyl, halo, hydroxyl, alkoxyl, aralkoxyl, aryloxyl, mercapto, mercaptoalkyl, carboxyl, acyloxyl, alkyloxycarbonyl, aryloxycarbonyl, aralkoxycarbonyl, acylamino, carbamoyl, alkylcarbamoyl, dialkylcarbamoyl,

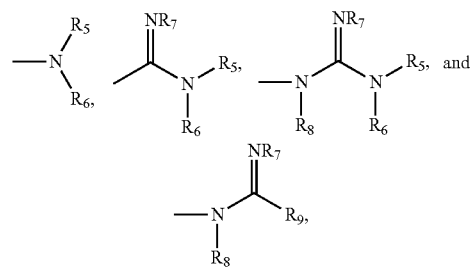

wherein $R_5$, $R_6$, $R_7$, $R_8$, and $R_9$ are independently selected from H, alkyl, aralkyl, and aryl;

or a pharmaceutically acceptable salt thereof.

In some embodiments, $D_{27}$, $D_{28}$, and $D_{29}$ are independently hydroxyl or alkoxyl. In some embodiments, the compound of Formula (XI) is

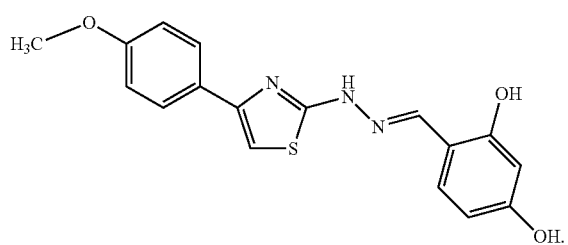 [SMILES: COc1ccc(-c2csc(N/N=C/c3ccc(O)cc3O)n2)cc1]

The compounds disclosed herein can also encompass derivatives of a parent compound, which has binding and/or modulation specificity for a TrkB receptor molecule, wherein the derivative also has binding and/or modulation specificity for the TrkB receptor. The derivative can exhibit enhancement in at least one of the characteristics selected from the group consisting of hydrophilicity, lipophilicity, amphipathicity, solubility, bioavailability, and resistance to hepatic degradation, as compared to the parent compound.

In some embodiments, the compound is a derivative of a parent compound having binding and/or modulation specificity for a TrkB receptor molecule, wherein the derivative is transformed in vivo to the parent compound or to another derivative of the parent compound that also has binding and/or modulation specificity for the TrkB receptor. Such derivatives can be referred to in some embodiments as prodrugs. Prodrugs can contain bonds that hydrolyze in vivo chemically (i.e., hydrolysis catalyzed by changes in pH) or enzymatically. Such bonds include, but are not limited to, esters, amides, and carbonates. Hydrolysis of such a bond in vivo can reveal, for example, a hydrogen donor moeity, such as an alcohol or an amine.

It is to be understood that in some embodiments the compounds disclosed herein can encompass a pharmacophore substantially identical to the pharmacophore illustrated in FIG. 1. Representative such compounds include, but are not limited to, compounds encompassed by Formulae (I-XI).

II.B. Formulations

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in *Remington: The Science and Practice of Pharmacy*, A. Gennaro, ed., 20th edition, Lippincott, Williams & Wilkins, Philadelphia, Pa.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Further, formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

Formulations of the compounds can contain minor amounts of wetting or emulsifying agents, or pH buffering agents. The formulations comprising the compound can be a liquid solution, suspension, emulsion, tablet, pill, capsule, sustained release formulation, or powder.

The compounds can be formulated as a suppository, with traditional binders and carriers such as triglycerides.

Oral formulations can include standard carriers such as pharmaceutical grades of mannitol, lactose, starch, magnesium stearate, polyvinyl pyrollidone, sodium saccharine, cellulose, magnesium carbonate, etc.

The pharmaceutical formulations comprising the compounds of the presently disclosed subject matter can include an agent which controls release of the compound, thereby providing a timed or sustained release compound.

II.C. Carriers

Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions.

Examples of non-aqueous solvents suitable for use in the presently disclosed subject matter include, but are not limited to, propylene glycol, polyethylene glycol, vegetable oils such as olive oil, and injectable organic esters such as ethyl oleate.

Aqueous carriers suitable for use in the presently disclosed subject matter include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the presently disclosed subject matter can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the presently disclosed subject matter include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the presently disclosed subject matter include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Parenteral carriers suitable for use in the presently disclosed subject matter include, but are not limited to, sodium chloride solution, Ringer's dextrose, dextrose and sodium chloride, lactated Ringers and fixed oils. Intravenous carriers include fluid and nutrient replenishers, electrolyte replenishers such as those based on Ringers dextrose and the like. Preservatives and other additives can also be present, such as, for example, antimicrobials, antioxidants, chelating agents, inert gases and the like.

Carriers suitable for use in the presently disclosed subject matter can be mixed as needed with disintegrants, diluents, granulating agents, lubricants, binders and the like using conventional techniques known in the art. The carriers can also be sterilized using methods that do not deleteriously react with the compounds, as is generally known in the art.

II.D. Salts

It is also to be understood that the disclosed compounds can further comprise pharmaceutically acceptable salts.

Such salts include, but are not limited to, pharmaceutically acceptable acid addition salts, pharmaceutically acceptable base addition salts, pharmaceutically acceptable metal salts, ammonium and alkylated ammonium salts.

Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like.

Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like.

Examples of metal salts include lithium, sodium, potassium, magnesium salts and the like.

Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

II.E. Tracers

In some embodiments of the presently disclosed subject matter, the BDNF mimetic comprises a tracer or label that can be detected in vivo (i.e., in a living subject) or in vitro (i.e., outside a living subject). In some embodiments, the tracer is detectable in vivo by a non-invasive method, including, but not limited to, scintigraphic methods, magnetic resonance imaging, ultrasound, or fluorescence. The tracer can be conjugated or otherwise associated with a BDNF mimetic, a drug carrier, or combinations thereof. Following administration of the labeled composition to a subject, and after a time sufficient for localization in vivo, the biodistribution of the composition can be visualized. For example, a BDNF mimetic labeled with a radioactive tracer can be used to detect tumors or other pathological states with altered TrkB expression in vivo.

In some embodiments, the label is detectable by a scintigraphic imaging method. Scintigraphic imaging methods include SPECT (Single Photon Emission Computed Tomography), PET (Positron Emission Tomography), gamma camera imaging, and rectilinear scanning. A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems comprise an array of detectors in a ring that also detect radioactivity in multiple dimensions.

When scintigraphic imaging is employed, the detectable tracer or label can comprise a radionuclide label selected from the group consisting of, but not limited to, $^{18}$fluorine, $^{64}$copper, $^{65}$copper, $^{67}$gallium, $^{68}$gallium, $^{77}$bromine, $^{80m}$bromine, $^{95}$ruthenium, $^{97}$ruthenium, $^{103}$ruthenium, $^{105}$ruthenium, $^{99m}$technetium, $^{107}$mercury, $^{203}$mercury, $^{123}$iodine, $^{124}$iodine, $^{125}$iodine, $^{126}$iodine, $^{131}$iodine, $^{133}$iodine, $^{111}$indium, $^{113}$mindium, $^{99m}$rhenium, $^{105}$rhenium, $^{101}$rhenium, $^{186}$rhenium, $^{188}$rhenium, $^{121}$mtellurium, $^{122m}$tellurium, $^{125m}$tellurium, $^{165}$thulium, $^{167}$thulium, $^{168}$thulium, and nitride or oxide forms derived there from.

Methods for radionuclide-labeling of a molecule so as to be used in accordance with the disclosed methods are known in the art. For example, a BDNF mimetic can be derivatized so that a radionuclide can be bound directly to it. Thus, the radionuclide can take the place of a hydrogen atom of one of the BDNF mimetics described herein in Formulas (I-XI). Alternatively, the radionuclide or radioactive tracer can be bound to a BDNF mimetic of Formulas (I-XI) through a suitable organic tether moiety, such as an alkylene group.

When compositions comprising radionuclides are used, stabilizers to prevent or minimize radiolytic damage, such as ascorbic acid, gentisic acid, or other appropriate antioxidants, can be added to the composition comprising the labeled targeting molecule.

III. Methods of Use

The presently disclosed subject matter provides novel methods of treating disorders, including, but not limited to, neurological disorders (e.g., neurodegenerative disorders) and in a subject. More particularly, the methods of the presently disclosed subject matter involve the administration of a compound having binding and/or modulation specificity for a TrkB receptor molecule in a subject to treat a disorder. The compound can be administered in an amount effective to induce survival signaling and/or to upregulate neural function. The compound can also be used to stimulate desired mechanisms of non-neural cells. The compound can also be used to partially or fully block endogenous BDNF.

The disorder to be treated can be any condition that is mediated, at least in part, by binding of neurotrophins to the TrkB receptor, and conditions wherein the TrkB receptor is present, though not necessarily causally linked to the condition. Neurotrophins can be present or absent in the condition. Such disorders include, but are not limited to, Alzheimer's disease, Huntington's disease, amyotrophic lateral sclerosis (ALS), Rett syndrome, epilepsy, Parkinson's disease, spinal cord injury, stroke, hypoxia, ischemia, brain injury, diabetic neuropathy, peripheral neuropathy, nerve transplantation complications, multiple sclerosis, peripheral nerve injury, conditions involving degeneration or dysfunction of cells expressing TrkB. The disorder to be treated further includes depression, obesity, and ischemic conditions of peripheral tissues. Table 1 lists a variety of disorders to which TrkB involvement has been linked.

TABLE 1

Disorders involving TrkB signaling.

| Pathological state potentially involving BDNF mechanisms | Potential roles for TrkB small molecule ligands | Reference(s) |
| --- | --- | --- |
| Alzheimer's disease | Agonist to compensate for BDNF deficiency, prevent neural degeneration, improve synaptic transmission, promote plasticity, promote neurogenesis | Fumagalli et al., 2005; Elliott et al., 2005 |
| Huntington's disease | Agonist to compensate for BDNF deficiency and to promote striatal neuron function | Canals et al., 2004; Cattaneo et al., 2005 |
| Parkinson's disease | Agonist to upregulate D3 receptor expression and to protect dopaminergic neurons | Guillin et al., 2003; Presgraves et al., 2004 |
| Rett syndrome | Agonist to compensate for BDNF deficiency | Sun and Wu, 2006 |
| Motor neuron disease | Agonist to inhibit motor neuron death | BDNF Study Group, 1999 |
| Depression | Agonist to promote neurogenesis or upregulate neurotransmitter function | Schechter et al., 2005 |
| Ischemic stroke | Agonist to prevent neuronal death and/or to upregulate neuronal function and promote post-injury plasticity | Schabitz et al., 2004; Nomura et al., 2005; Wu et al., 2005 |
| HIV dementia | Agonist to protect neurons from HIV-1/gp120-induced death | Mocchetti and Bachis, 2004 |
| Multiple sclerosis | Agonist to mimic immune-mediated BDNF protective mechanisms in MS lesions | Gielen et al., 2003; Stadelmann et al., 2005 |
| Spinal cord injury | Agonist to promote axonal regeneration, plasticity and activation of TrkB without p75$^{NTR}$ liganding to overcome myelin inhibition | Koda et al., 2004; Williams et al., 2005 |
| Nerve injury | Agonist to prevent post-axotomy neuron loss and/or promote regeneration | Watabe et al., 2005; Vogelin et al., 2006 |
| Hearing loss | Agonists to protect auditory neurons | McGuinness and Shepherd, 2005 |
| Obesity, diabetes, and metabolic syndrome | Agonist to limit food intake and correct metabolic syndrome | Wisse and Schwartz, 2003; Nakagawa et al., 2003; Lebrun et al., 2006 |
| Peripheral tissue ischemia | Agonist to promote angiogenesis | Kermani et al., 2005 |
| Epilepsy | Antagonist or partial agonist to inhibit hyperexcitable circuits in injured brain | He et al., 2005; Koyama and Ikegaya, 2005 |
| Pain | Antagonist, partial agonist or agonist to suppress pain transmission | Malcangio and Lessmann, 2003 |
| Cancer | Agonist or partial agonist to inhibit TrkB-dependent tumor therapeutic resistance mechanisms | Desmet and Peeper, 2006 |

The presently disclosed subject matter further provides for methods of facilitating cell survival or function, including both neural cells and non-neural cells. Representative neural cells include, but are not limited to, hippocampal pyramidal cells, cortical cells, striatal cells, substantial nigra cells, motor neuron cells, Purkinje cells, dorsal root ganglia cells. Non-neuronal cells include, but are not limited to, vascular endothelial cells. The methods can comprise treating a neural or non-neural cell with a compound having binding or modulation specificity for a TrkB receptor molecule, whereby the compound induces survival signaling and/or upregulation of cell function.

The BDNF mimetics of Formulas (I-XI) can be used in both in vivo and in vitro settings. In some embodiments, the BDNF mimetics can be used as a cost saving alternative to BDNF in in vitro methods. In some embodiments, the BDNF mimetics can be used in methods related to stem cells. Thus, in some embodiments, the BDNF mimetics can be used for maintaining stem cells in an undifferentiated state or to induce stem cell differentiation. By way of example, a BDNF mimetic as disclosed herein can be used in methods currently available in the art that employ BDNF (Huang, E. J., Reichardt, L. F. (2003) *Annu Rev Biochem* 72, 609-642; Banker, G., Goslin, K. (Eds.) (1998) *Culturing Nerve Cells*, Chapters 10 and 14 (Cambridge, Mass.: The MIT Press)), except with the substitution of the BDNF mimetic.

III.A. Administration

The presently disclosed subject matter provides methods of administering compounds having binding and/or modulation specificity for a TrkB receptor compound in order to ameliorate a disorder mediated by TrkB binding or modulation in a subject. The method can comprise administering to a subject an effective amount of a compound having binding and/or modulation specificity for a TrkB receptor, such as any of the compounds disclosed herein.

As used herein, administering can be effected or performed using any of the various methods known to those skilled in the art. The compound can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles.

Further, the presently disclosed compounds can be administered to a localized area in need of treatment. This can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

The form in which the compound is administered (e.g., syrup, elixir, capsule, tablet, solution, foams, emulsion, gel, sol) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. The compounds and agents disclosed herein can be administered together with other biologically active agents, such as analgesics, anti-inflammatory agents, anesthetics and other agents which can control one or more symptoms or causes of a TrkB mediated disorder.

Additionally, administration can comprise administering to the subject a plurality of dosages over a suitable period of time. Such administration regimens can be determined according to routine methods, upon a review of the instant disclosure.

In some embodiments, administration comprises administering to the subject a dose or plurality of dosages to achieve a compound concentration in a cell or in a cell microenvironment of between about 0.10 μM and about 50 μM.

The compounds of the presently disclosed subject matter can be employed as the sole active agent in a pharmaceutical or can be used in combination (e.g., administered proximate in time to each other or even in the same formulation) with other active ingredients, e.g., neurotrophins, or other factors or drugs which can facilitate neural survival or axonal growth in neurodegenerative diseases. For example, synergistic effects can be provided by administering a compound having binding and/or modulation specificity for a TrkB receptor molecule to a subject with a second compound having binding and/or modulation specificity for a $p75^{NTR}$ receptor molecule. Representative compounds having binding specificity for $p75^{NTR}$ receptor molecules are disclosed in U.S. patent application Ser. No. 11/396,936, filed Apr. 3, 2006, herein incorporated by reference in its entirety.

III.B. Dosage

For administration of a compound as disclosed herein, conventional methods of extrapolating human dosage based on doses administered to a murine animal models can be carried out using the conversion factor for converting the mouse dosage to human dosage: Dose Human per kg=Dose Mouse per kg×12 (Freireich et al., (1966) *Cancer Chemother Rep.* 50, 219-244). Drug doses can also be given in milligrams per square meter of body surface area rather than body weight, as this method achieves a good correlation to certain metabolic and excretionary functions. Moreover, body surface area can be used as a common denominator for drug dosage in adults and children as well as in different animal species (Freireich et al., (1966) *Cancer Chemother Rep.* 50, 219-244). Briefly, to express a mg/kg dose in any given species as the equivalent mg/sq m dose, the dosage is multiplied by the appropriate km factor. In an adult human, 100 mg/kg is equivalent to 100 mg/kg×37 kg/sq m=3700 mg/m².

Insofar as the compounds disclosed herein can take the form of a mimetic or fragment thereof, it is to be appreciated that the potency, and therefore dosage of an effective amount can vary. However, one skilled in the art can readily assess the potency of a compound of the type presently envisioned by the presently disclosed subject matter.

The compounds disclosed herein can be used in unit dosage form and can be prepared by any of the methods well known in the pharmaceutical art, or example, as described in *Remington's Pharmaceutical Sciences* (Mack Pub. Co., Easton, Pa., 1980).

It will be appreciated by one of skill in the art that dosage range will depend on the particular compound, and its potency. The dosage range is understood to be large enough to produce the desired effect in which the neurological disorder and the symptoms associated therewith are ameliorated and/or survival of the neural cells is achieved, but not be so large as to cause unmanageable adverse side effects. The appropriate range for therapeutic effectiveness will be readily determined by one skilled in the art depending on the route of administration, age, and condition of the subject being treated. The dosage can also be adjusted by the individual physician in the event of any complication. No unacceptable toxicological effects are expected when compounds disclosed herein are used in accordance with the presently disclosed subject matter.

An effective amount of the compounds disclosed herein comprise amounts sufficient to produce a measurable biological response. Actual dosage levels of active ingredients in a therapeutic compound of the presently disclosed subject matter can be varied so as to administer an amount of the active compound that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Further with respect to the methods of the presently disclosed subject matter, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the presently disclosed subject matter indicate effectiveness with respect to all vertebrate species which are to included in the term "subject." In this context, a vertebrate is understood to be any vertebrate species in which treatment of a neurodegenerative disorder is desirable. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos or as pets (including parrots), as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

III.C. Coatings

In some embodiments, the compounds of the presently disclosed subject matter can be used in coatings. For example, the BDNF mimetics of Formulas (I-XI) can be used to coat medical devices, such as surgical tools, biosensors, and implants, to promote neural and/or non-neural cell survival in tissues or fluids coming into contact with the medical device or to treat a pathological state with altered TrkB expression in an area in contact with the medical device. In some embodiments, the medical device is a cochlear implant, an electronic device interfacing with the nervous system, or a synthetic matrix designed to support neural regeneration.

The mimetics can be coated onto the medical devices by a variety of methods. For example, the mimetics can be suspended or dissolved in a liquid carrier, coated and dried onto the medical device. Alternatively, the mimetics can be conjugated to a chemically functionalized surface of a device or imbedded in or conjugated to a polymeric coating of a medical device. In some embodiments, the device being coated can have a metallic surface, such as, for example, stainless steel, nickel, titanium, aluminum, copper, gold, silver, platinum, and combinations thereof. In some embodiments, the device can have a glass or polymeric surface.

EXAMPLES

The following Examples have been included to provide illustrations of the presently disclosed subject matter. In light of the present disclosure and the general level of skill in the art, those of skill will appreciate that the following Examples are intended to be exemplary only and that numerous changes, modifications and alterations can be employed without departing from the spirit and scope of the presently disclosed subject matter.

Materials and Methods for Examples

Computational Studies

Computational studies were performed using the Accelrys Catalyst® and INSIGHT II™ systems obtained from Accelerys (San Diego, Calif., United States of America).

Antibodies and Proteins

Monoclonal anti-phospho-ERK$^{T202/Y204}$, polyclonal anti-ERK42/44, monoclonal anti-phospho-AKT$^{S473}$, polyclonal anti-AKT, polyclonal anti-phospho-NFκB-p65(Ser$^{563}$), and site-specific polyclonal anti-Trk$^{Y490}$ were obtained from Cell Signaling Technology, Inc. (Beverly, Mass., United States of America). Monoclonal anti-actin was obtained from Sigma-Aldrich Corp. (St. Louis, Mo., United States of America). Polyclonal TrkA and TrkB antibodies were obtained from Upstate USA, Inc. (Charlottesville, Va., United States of America). Recombinant human NGF was obtained from Invitrogen (Carlsbad, Calif., United States of America) and BDNF from Sigma-Aldrich (St. Louis, Mo., United States of America).

Hippocampal neurons were prepared from E16-17 mouse embryos as previously described (Yang, T. et al. (2003) *J Neurosci* 23, 3353-3363). Low density cultures were initiated in poly-L-lysine coated A/2 plates by adding 25 µl of cell suspension (2000 neurons/well; 12,500 cells/cm$^2$), 25 µl of DMEM containing 10% FBS, and different concentrations of recombinant BDNF, NGF, or TrkB-binding compounds to each well.

After 48 hours in culture, cell survival was assessed as previously described (Longo, F. M., Manthorpe, M., Xie, Y. M., Varon, S. (1997) *J Neurosci Res* 48, 1-17) using a combination of standard morphological criteria along with visual determination of whether a given cell converted MTT to its blue formazan product. Briefly, the number of surviving neurons was determined by counting the total number of cells in each well that were both morphologically intact and filed with blue product (Longo F. M., Manthorpe, M., Xie, Y. M., Varon, S. (1997) *J Neurosci Res* 48, 1-17). For each neurotrophin or compound concentration, duplicate wells were counted and the resulting values averaged. Activity of each compound was confirmed by blinded counts. Counts were normalized to survival achieved with 25 ng/ml BDNF or to baseline survival. Fitting of dose-responsive curves was performed with SIGMAPLOT™ obtained from SYSTAT Software Inc. (Richmond, Calif., United States of America).

For signaling pathway inhibitor studies, LY294002, PD98059 (obtained from EMD Biosciences/Calbiochem, San Diego, Calif., United States of America), were added to cultures at final concentrations of 25 µM, 50 µM, and 2.5 µg/ml respectively, concomitantly with BDNF or TrkB-binding compounds. For all studies applying signaling inhibitors, survival was assessed at 48 hours.

Protein Extraction and Western Blot Analysis

For assays of Trk, AKT, and ERK activation, hippocampal neurons derived from E16-17 mice were cultured in poly-L-lysine coated six-well plates (Corning, Inc., Corning, N.Y., United States of America) in DMEM containing 10% FBS, followed by incubation in serum-free DMEM for 2 hours before addition of neurotrophins or compounds. At the indicated time points, neurons were harvested in lysis buffer consisting of: 20 mM Tris, pH 8.0, 137 mM NaCl, 1% Igepal CA-630, 10% glycerol, 1 mM PMSF, 10 µg/ml aprotinin, 1 µg/ml leupeptin, 500 µM orthovanadate (Zhou, J., Valletta, J. S., Grimes, M. L., Mobley, W. C. (1995) *J Neurochem* 65, 1146-1156). Lysates were centrifuged, the supernatant collected, and protein concentrations determined using the BCA Protein Assay Reagent obtained from Pierce (Rockford, Ill., United States of America).

Western blots were performed as described previously (Yang, T. et al. (2003) *J Neurosci* 23, 3353-3363). Western blot signals were detected using the ECL Chemiluminescence System obtained by Amersham (Piscataway, N.J., United States of America) (Yang, T. et al. (2003) *J Neurosci* 23, 3353-3363). To detect the presence of anti-Trk antibodies, blots were probed with horseradish peroxidase-linked goat anti-rabbit IgG obtained from Amersham/Pharmacia Biotech (Piscataway, N.J., United States of America). Signals were detected by the ECL chemiluminescence system obtained from Amersham Biosciences (Piscataway, N.J., United States of America). To control for variation in protein loading, the blot was stripped and reprobed with β-actin monoclonal antibody obtained from Sigma (St. Louis, Mo., United States of America).

Example 1

Computational Modeling, Pharmacophore Generation, Virtual and Functional Screening In order to generate a productive pharmacophore emulating a loop structure known to interact with a receptor, it was hypothesized that (1) the degrees of freedom of the ligand peptide structure are restricted by its residence in the protein, and (2) there is little "induced fit" involving changes in loop structure at the targeted receptor subsite, or it is accommodated by flexibility of the small molecule ligand. When both of these conditions apply, they allow an interacting/activating small molecule conformation that interacts with the receptor in a manner similar to that of the native ligand.

Efforts were focused on locating compounds emulating a single loop BDNF loop 2 structure. Computational studies suggested that in situ, the tethered loop 2 backbone and proximal portions of the side chain structure had restricted degrees of freedom, and an intermediate structure chosen from an ensemble of samples from loop molecular dynamics simulations was extracted and used to build a pharmocophoric model. The residues involved with the pharmacophore were Ser45, Lys46 and Gln48 of BDNF (FIG. 1). Guidance for the placement of pharmacophore features was obtained from consideration of loop phylogeny and side chain chemistry.

An average of 35 conformers of each of over 5.5 million compounds compounds were screened against the pharmacophore, yielding approximately 3000 that fit with a calculated internal energy of less than 10 kcal/mol. This number was reduced to approximately 50 by visual inspection, calculated blood brain barrier penetration and other predicted medicinal properties on the basis of likely steric compatibility with a hypothetical shallow receptor binding pocket, and maximal flexibility of the functional groups.

Example 2

Compounds Promote Hippocampal Neuron Survival

High-throughput virtual screening based on BDNF loop 2 models (FIG. 1) and small-scale in vitro bioassays were used to identify chemically diverse compounds with potent neurotrophic activity. Approximately 5.5 million compounds were screened in silico to produce a high yield of 15 positives out of 32 compounds submitted to in vitro screening (47%).

In order to understand the mechanisms of action of the BDNF loop 2 mimetics and to test the conjecture that they work via the targeted receptor, TrkB, the dose-dependent relationships of the survival-promoting activities of the mimetics was compared to BDNF using embryonic hippocampal neurons in culture conditions in which BDNF promotes neural survival. In the cultures, neurotrophic activity was mediated by BDNF principally through TrkB and p75$^{NTR}$ as they express little TrkA (Brann, A. B., et al. (1999) *J Neurosci* 19, 8199-8206; Bui, N. T., et al. (2002) *J Neurochem* 81, 594-605).

Figure 2:
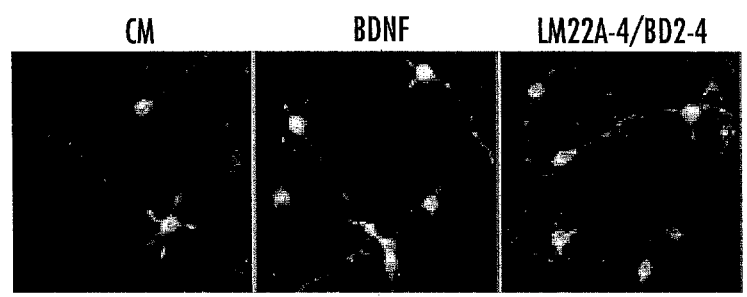
FIG. 2 is a series of fluorescence photomicrographs of E16 mouse hippocampal neuronal cultures treated with culture medium only (CM) or medium containing BDNF or Compound 4 (also referred to in the figures as LM22A-4 and BD2-4), showing that Compound 4 has neurotrophic effects similar to that of BDNF. Neurons are immunostained with GAP43 antibody.
Figure 3A:
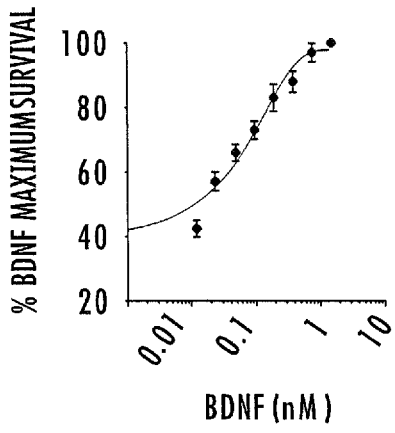
FIGS. 3A-3E are a series of neuron survival dose response curves of BDNF (FIG. 3A), Compound 1 (also referred to as BD2-1, FIG. 3B) Compound 2 (also referred to as BD2-2, FIG. 3C), Compound 3 (also referred to as BD2-3, FIG. 3D), and Compound 4 (also referred to as BD2-4, FIG. 3E) using Mouse E16 hippocampal neurons. Survival was determined as the total number of cells in each well that were both morphologically intact and filled with blue formazan MTT conversion product (Longo, F. M., Manthorpe, M., Xie, Y. M., and Varon, S. (1997) *J Neurosci Res.* 48, 1-17). Counts were normalized to survival achieved with 25 ng/mL BDNF. Survival was assessed at 48 hrs. Symbols and bars indicate mean+/−s.e.m., and lines are fits of a single exponential rise model to the data.
Figure 3B:
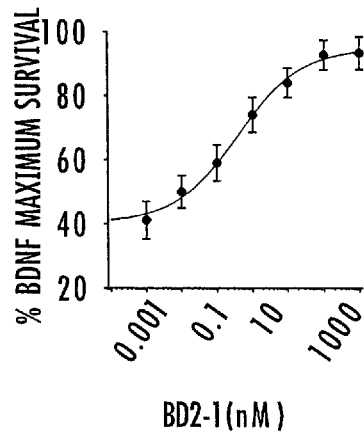
Figure 3C:
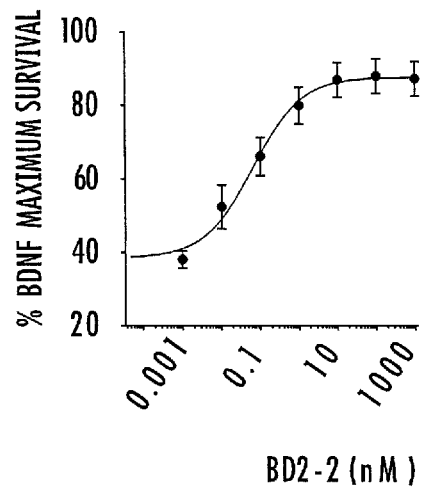
Figure 3D:
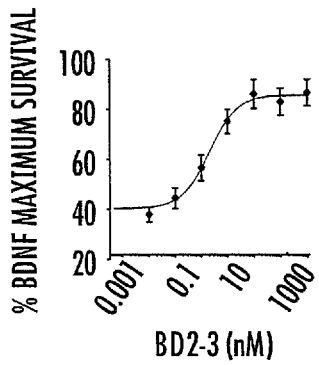
Figure 3E:
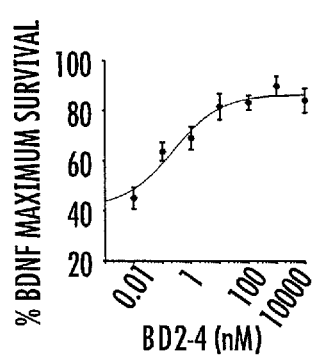
Figure 4:
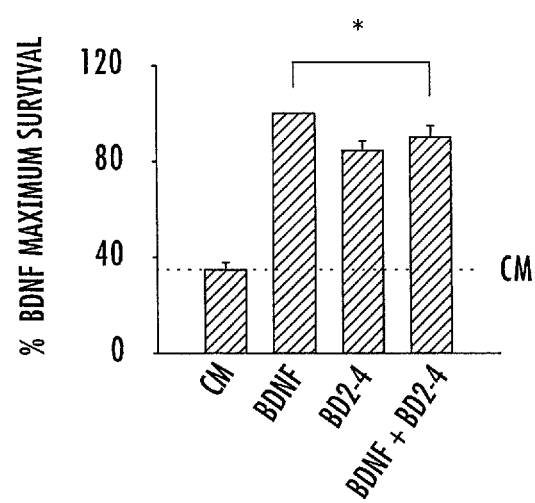
FIG. 4 is a bar graph comparing neuron survival (Mouse E16 hippocampal neurons) with no treatment (CM), treatment with BDNF (50 ng/mL), with Compound 4 (BD2-4), or with a combination of BDNF and Compound 4 (BDNF+BD2-4), showing that Compound 4 is a partial agonist of BDNF. This is the first observation that a small molecule BDNF mimetic can function as a partial agonist.

Studies indicated that Compound 4 (BD2-4) prevents the death of E16 hippocampal neurons and that neurite outgrowth length promoted by Compound 4 was similar to that seen with BDNF. See FIG. 2. Dose-response profiles of Compounds 1-4 (BD2-1, BD2-2, BD2-3, and BD2-4, respectively; FIG. 3A-E) demonstrated $EC_{50}$ values in the range of 0.1-1.0 nM and intrinsic activities of 50-200% of the BDNF response. Additionally, as predicted for a partial agonist, Compound 4 in the presence of a maximally effective BDNF concentration (50 ng/mL) causes an inhibition of BDNF activity. See FIG. 4. The structures of Compounds 1-4 are illustrated in Table 2 below.

TABLE 2

Structures of Compounds 1-4

| Compound No. | Structure |
| --- | --- |
| 1 (BD2-1) | 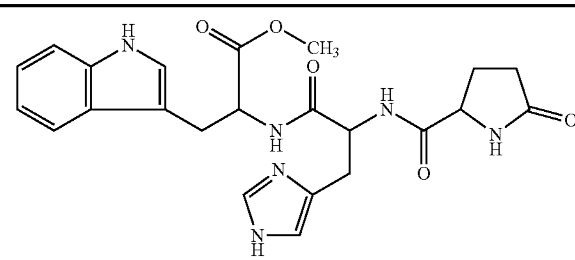 |
| 2 (BD2-2) | 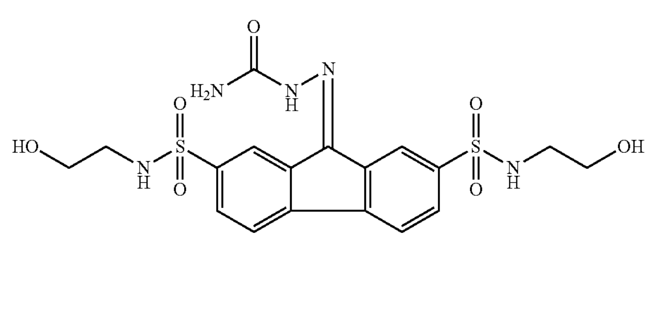 [SMILES: NC(=O)NN=C1c2cc(S(=O)(=O)NCCO)ccc2-c2ccc(S(=O)(=O)NCCO)cc21] |

TABLE 2-continued

Structures of Compounds 1-4

| Compound No. | Structure |
|---|---|
| 3 (BD2-3) | 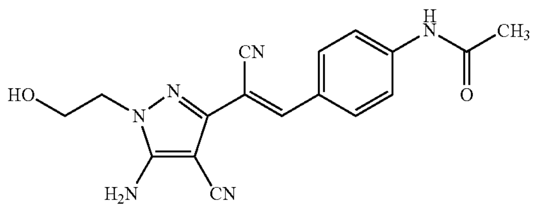 [SMILES: CC(=O)Nc1ccc(/C=C(\C#N)c2nn(CCO)c(N)c2C#N)cc1] |
| 4 (BD2-4) | 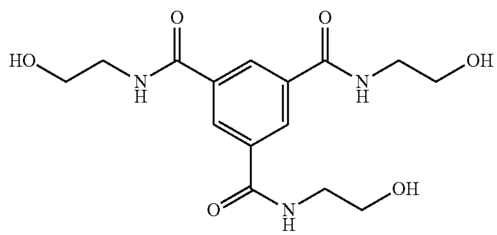 [SMILES: O=C(NCCO)c1cc(C(=O)NCCO)cc(C(=O)NCCO)c1] |
| 24 (BD2-24) | 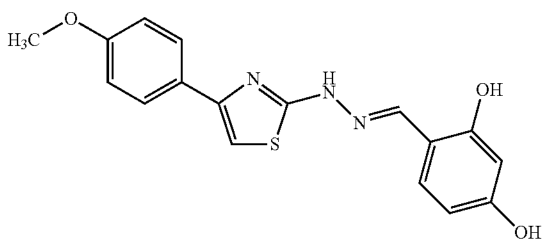 [SMILES: COc1ccc(-c2csc(N/N=C/c3ccc(O)cc3O)n2)cc1] |

Of the four compounds initially identified, one, Compound 4, is predicted to have the most "drug-like" character by the Lipinski criteria (Lipinski, C. A. (2000) *J Pharm Toxicol Methods* 44, 235-249) and blood-brain barrier calculations (Fu, X. C., Chen, C. X., Liang, W. Q., Yu, Q. S. (2001) *Acta Pharmacol Sin* 22, 663-668; Clark, D. E. (2002) *J Pharm Sci* 88, 815-821). As such, Compound 4 was selected for more detailed mechanistic study.

Example 3

Compounds Activate TrkB Receptors

In order to assess the interactions of the BDNF loop 2 mimetic compounds with TrkB receptors, the ability of Compound 4 to activate TrkA, TrkB, and TrkC was compared in a series of Western blotting experiments. These studies demonstrate that the BDNF mimetics achieve a high level of specificity in that only TrkB is activated.

Figure 5:
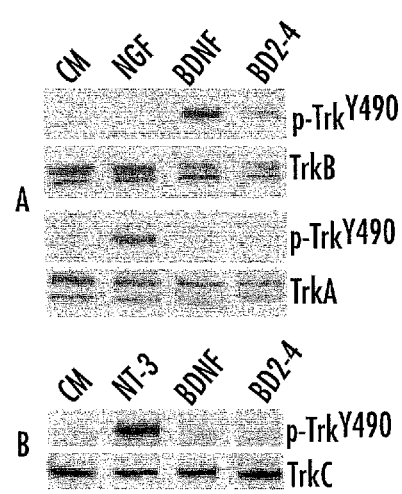
FIG. 5A is a digital composite image of Western blots monitoring Trk activation as indicated by promotion of Trk phosphorylation at Y490 in NIH3T3 cells expressing either TrkB (upper two panels) or TrkA (lower two panels) demonstrating that BDNF and Compound 4 (BD2-4) (as indicated above each lane in the blots) activate TrkB and not TrkA while NGF (second column from left) activates TrkA but not TrkB. The upper lane for each pair shows staining with anti-p-Trk$^{Y490}$ antibody (p-Trk$^{Y490}$), while the lower lane of each pair shows total TrkB or TrkA. CM represents culture medium.
FIG. 5B is a digital composite image of Western blots monitoring TrkC activation as indicated by promotion of Trk phosphorylation at Y490 in NIH3T3 cells expressing TrkC. BDNF and Compound 4 (BD2-4) (the right two lanes) do not activate TrkC, while NT-3 (second lane from the left) activates TrkC. CM represents culture medium.

The top two panels in FIG. 5A show that in NIH3T3 cells expressing TrkB, both BDNF and Compound 4 (BD2-4) activate TrkB as evidenced by Trk phosphorylation (indicated by probing with anti-Trk$^{Y490}$ antibodies in the uppermost panel). Culture medium alone (CM) or treatment with NGF does not activate TrkB. The second panel from the top shows the Western blot with anti-TrkB antibodies indicating the total amount of TrkB present. In the bottom two panels of FIG. 5A, NIH3T3 cells expressing TrkA were used. NGF promotes activation of TrkA as evidenced by Trk phosphorylation, but BDNF and Compound 4 do not.

In FIG. 5B, NIH3T3 cells expressing TrkC were used. The bottom panel indicates the total amount of TrkC present by probing with anti-TrkC antibodies. NT-3 promotes the phosphorylation of Trk (upper panel), while culture medium alone (CM), BDNF, and Compound 4 do not.

Example 4

Compound Activity in Huntington's Disease Model

Quinolinic acid-induced death of striatal neurons is an established model for Huntington's disease (HD). Previous work has shown that BDNF functions are impaired in HD and that administration of BDNF can prevent quinolinic acid-induced death. See Perez-Navarro, E., et al. (2000) *J. Neurochem* 75, 2190-2199; and Kells, A. P., et al. (2004) *Mol Ther* 9, 682-688, each of which is herein incorporated by reference in its entirety.

Figure 6A:
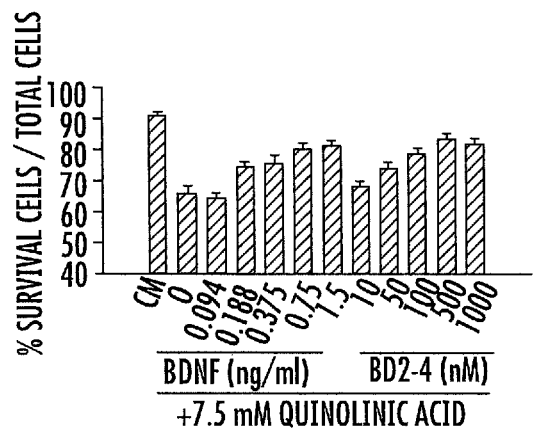
FIG. 6A is a bar graph showing prevention of quinolinic acid-induced death of mouse E16 striatal neurons by varying concentrations of BDNF and Compound 4 (BD2-4). The quinolinic acid-induced death is used as a model for neuronal death in Huntington's disease (HD). Application of quinolinic acid at 7.5 mM leads to death of approximately 50% of neurons as seen comparing culture medium alone (CM) to quinolinic acid in the absence of BDNF. Bars indicate mean±s.e.m.

As shown in FIG. 6A, application of quinolinic acid at 7.5 mM leads to death of approximately 50% of mouse E16 striatal neurons comparing culture medium alone (CM) to quinolinic acid in the absence of BDNF, over a dose range of 0 to 1.5 ng/mL, and BD2-4, over a dose range of 10-1000 nM, demonstrate similar efficacies in decreasing quinolinic acid-induced death.

Figure 6B:
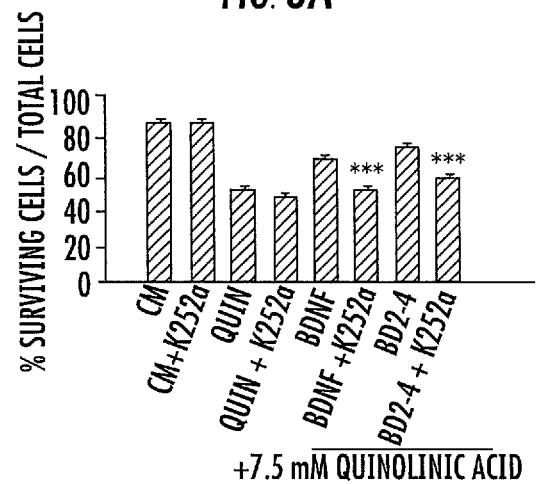
FIG. 6B is a bar graph showing the effects of K252a (a TrkB receptor activation inhibitor) on the prevention of quinolinic acid-induced death in mouse E16 striatal neurons by BDNF and Compound 4 (BD2-4). CM represents culture medium and QUIN represents quinolinic acid. Bars indicate mean±s.e.m and *** indicates $p<0.005$ student t test.

The K252a inhibitor is a well-characterized inhibitor of TrkB receptor activation. As shown in FIG. 6B, K252a had no effect on quinolinic acid-induced death but did block the ability of BDNF and BD2-4 to prevent death. These findings confirm that the BD2-4 effect is mediated through its ability to activate the TrkB receptor.

Figure 6C:
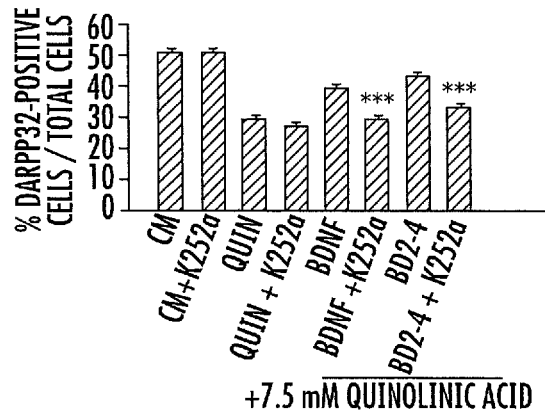
FIG. 6C is a bar graph of the results of a study similar to that described for FIG. 6B only using Darp32-positive neurons. Bars indicate mean±s.e.m and *** indicates $p<0.005$ student t test.

A study similar to the one shown in FIG. 6B was conducted in which only DARP32-positive neurons were assessed. DARP32-positive neurons represent the population within the striatum that are particularly vulnerable in HD. As shown in FIG. 6C, BD2-4 protects DARP32—positive neurons with an efficacy similar to that of BDNF. FIG. 6C further demonstrates that this protection is mediated through TrkB and that the efficacy of BD2-4 is similar to that of BDNF. As in FIG. 6B, the addition of the inhibitor K252a decreased the ability of BDNF and BD2-4 to prevent cell death (FIG. 6C).

Example 5

Compound Activity in Parkinson's Disease Model

Exposure of SH-SY5Y cells to 1-methyl-4-phenylpyridinium (MPP$^+$) with resulting cell death is a well-characterized model of Parkinson's disease (PD). See Presgraves, S. P., et al. (2004) *Exp Neurol* 190, 157-170, and Dluzen, D. E., et al. (2004) *Neuroscience* 128, 201-208, each of which is herein incorporated by reference in its entirety. BDNF has also been previously shown to protect dopaminergic neurons. Further, MPP$^+$ causes a PD-like condition in primates.

For the Parkinson's disease model assays, human SH-SY5Y cells were used after terminal differentiation into a dopaminergic phenotype (Presgraves, S. P., et al. (2004) *Exp Neruol* 190, 157-170). Human SH-SY5Y neuroblastoma cells were propagated to confluence in Dulbecco's Modified Eagle's media (DMEM) supplemented with 10% fetal calf serum, 100 µg/mL penicillin, 100 µg/mL streptomycin, 0.25 µg/mL amphotericin B, and 0.01 µM non-essential amino acids and then sub-cultured for differentiation. For differentiation, the cells were incubated in same media containing 10 µM retinoic acid for 3 days; then the media was removed and replaced with media containing 160 nM of the phorbol ester 12-O-tetradecanoyl-phorbol-13-acetate (TPA) for 3 days of differentiation. The cells were then administered a range dose of BD2-4 or BDNF ($1\times10^{-12}$ M to 1 mM) in DMEM for 30 mins for three days prior to addition of 100 µM MPP$^+$. Following transfer of MPP$^+$ to the media, sister cultures were tested at 6, 12, 24, and 48 hrs for the cytotoxicity of MPP$^+$ as measured by the MTT and lactate dehydrogenase method (LDH) assays which accurately measure different aspects of cell death. In addition, the neuroprotective effects of a fixed dose of BD2-4 and BDNF on MPP$^+$ induced cell death were tested in the presence and absence of TrkB inhibitor K252a (200 nM).

Figure 7:
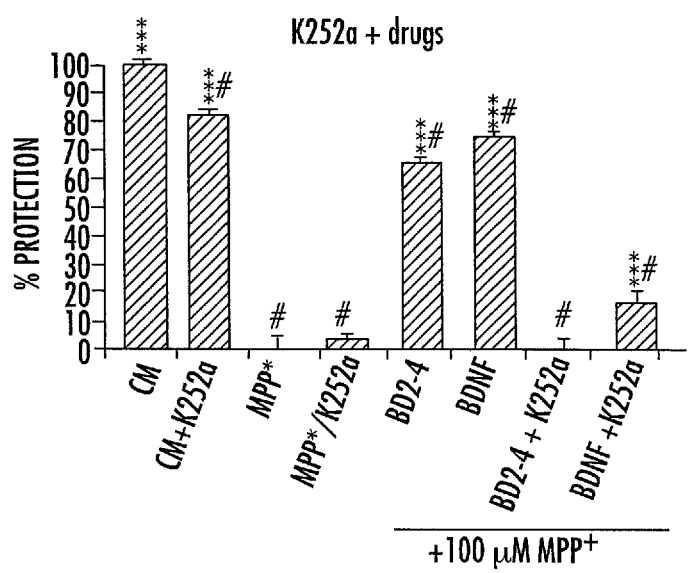
FIG. 7 is a bar graph showing that BDNF mimetics prevent neuronal death in a Parkinson's disease (PD) model. As indicated by the bar second from the left, the TrkB inhibitor K252a has a small effect on lowering cell survival in the SH-SY5Y neuroblastoma cells compared to cells treated with culture medium (CM) alone. The neurotoxin 1-methyl-4-phenylpyridinium (MPP$^+$, 100 μM) promotes death of essentially all cells. The death-inducing activity of MPP$^+$ is significantly blocked to a similar extent by BDNF and BD2-4 (Compound 4). K252a blocks the protection effect of BDNF and BD2-4 (the two bars on the right of the graph) indicating that this protective effect is mediated through the activation of TrkB. Mean±SE are shown. One-Way ANOVA showed significant effects between drug conditions ($F=648.2$, $P<0.0001$). ***$P<0.001$ vs MPP$^+$, # $P<0.001$ vs CM.

As shown in FIG. 7, the TrkB inhibitor K252a has a small effect on lowering cell survival of dopaminergic neurons. MPP$^+$ promotes death of essentially all cells. The death-inducing activity of MPP$^+$ is significantly blocked to a similar extent by both BDNF and BD2-4. K252a blocks a significant amount of the protection afforded by BDNF and BD2-4, indicating that this protective effect is mediated through the activation of TrkB. Mean±SE are shown.

Example 6

Compound Activity in Alzheimer's Disease Model

The ability of the BDNF mimetics to prevent Aβ-induced neuronal degeneration was tested as a model of the compounds' ability to treat Alzheimer's disease. E16-17 hippocampal neurons were matured for 6 days and then incubated for 3 days with the indicated combinations of AR oligomer preparations (Dahlgren, K. N., et al. (2002) *J Biol Chem* 277, 32046-32053), neurotrophins and neurotrophin mimetics. Following the three day incubation, neuronal survival was assessed using standard morphological criteria (Massa, S. M., et al. (2006) *J Neurosci* 26, 5288-5300.).

Figure 8:
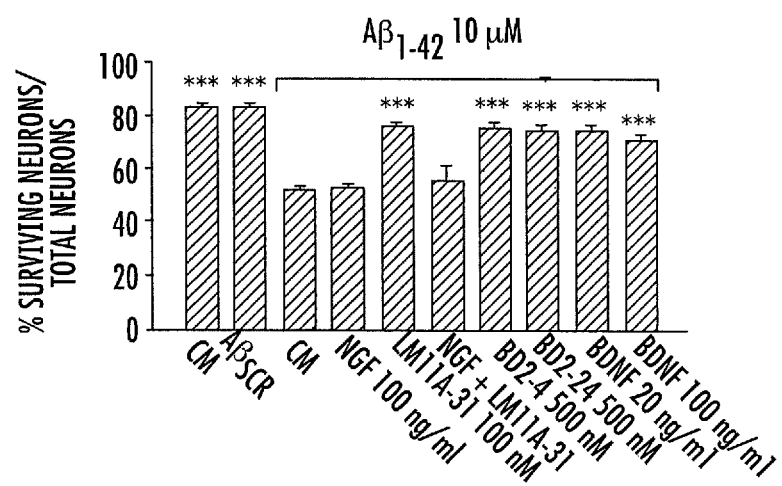
FIG. 8 is a bar graph showing that BDNF and BDNF mimetics prevent Aβ-induced neuronal degeneration in E16-17 hippocampal neurons. Neuronal cell survival in culture medium (CM) and with the addition of 10 μM Aβ$_{Scrambled}$ oligomer are shown in the two bars on the left-hand side of the graph as positive controls. Cells were also treated with 10 μM Aβ$_{1-42}$ alone or in combination with NGF (100 ng/mL), NGF mimetic LM11A-31 (100 nM), a combination of NGF and LM11A-31, Compound 4 (BD2-4, 500 nM), Compound 24 (BD2-24, 500 nM), or either 20 or 100 ng/mL BDNF, as indicated under each bar. Addition of Aβ$_{1-42}$ oligomer but not control Aβ$_{Scrambled}$ oligomer resulted in an approximate 40% reduction in neuronal survival. BDNF mimetics BD2-4 and BD2-24 were as effective as BDNF in blocking Aβ-induced degeneration. Mean+SE are shown and ***$p<0.001$ for survival above CM baseline.

As shown in FIG. 8, addition of Aβ$_{1-42}$ oligomer (10 µM) but not control Aβ$_{Scrambled}$ oligomer AR (10 µM) resulted in an approximate 40% reduction in neuronal survival. NGF failed to prevent Aβ-induced degeneration. NGF mimetic LM11A-31, known to act as a ligand at the NGF p75$^{NTR}$ receptor (described in U.S. patent application Ser. No. 11/396,936, filed Apr. 3, 2006), blocked Aβ-induced degeneration. This blocking activity was itself blocked by NGF, consistent with NGF competing with LM11A-31 at the p75$^{NTR}$ receptor and thereby inhibiting its protective effect. BDNF mimetics BD2-4 (Compound 4) and BD2-24 (Compound 24) were as effective as BDNF in blocking Aβ-induced degeneration. These studies demonstrate for the first time that BDNF can block Aβ oligomer-induced degeneration and that BDNF mimetics are equally as effective in blocking the Aβ oligomer-induced degeneration as BDNF protein.

REFERENCES

The references listed below as well as all references cited in the specification are incorporated herein by reference to the extent that they supplement, explain, provide a background for or teach methodology, techniques and/or compounds employed herein.

Appel, S. H. (1981) *Ann Neurol* 10, 499.
Banker, G., Goslin, K. (Eds.) (1998) Culturing Nerve Cells, Chapters 10 and 14 (Cambridge, Mass.: The MIT Press).
Beattie, M. S., et al. (2002) *Neuron* 36, 375-386.
Canals, J. M., et al. (2004) *J Neurosci* 24, 7727-7739.
Carter, B. D., et al. (2002) *Science* 272, 542-545.
Casaccia-Bonnefil, P., et al. (1996) *Nature* 386, 716-719.
Cattaneo, E., et al. (2005) *Nat Rev Neurosci* 6, 919-930.
Clark, D. E. (2002) *J Pharm Sci* 88, 815-821.
Dahlgren, K. N., et al. (2002) *J Biol Chem* 277, 32046-32053.
Desmet, C. J., Peeper D. S. (2006) *Cell Mol Life Sci* 63, 755-759.
Dluzen, D. E., et al. (2004) *Neuroscience* 128, 201-208
Elliot E., et al. (2005) *Eur J Neurosci* 22, 1081-1089.
Fahnestock, M., et al. (2001) *Mol Cell Neurosci* 18, 210-220.
Foehr, E. D., et al. (2003) *J Neurosci Res* 73, 7556-7563.
Freireich et al., (1966) *Cancer Chemother Rep.* 50, 219-244.
Fu, X. C., et al. (2001) *Acta Pharmacol Sin* 22, 663-668.
Fumagalli, F., et al. (2005) *The Pharmacogenomics J,* 1-8.
Gentry, J. J., Casaccia-Bonnefil, P., Carter, B. D. (2000) *J Biol Chem* 275, 7558-7565.
Gielen, A., et al. (2003) *Scan J Imm* 57, 493-497.
Guillin, O., et al. (2003) *Eur J Pharm* 480, 89-95.
Harrington, A. W. et al. (2004) *Proc Natl Acad Sci USA* 101, 6226-6230.
Harrington, A. W, Kim, J. Y., Yoon, S. O. (2002) *J Neurosci* 22, 156-166.
He, X. P., et al. (2004) *Neuron* 43, 31-42.
Huang, C. S. et al. (1994) *J Biol Chem* 274, 36707-36714.
Huang, E. J., Reichardt, L. F. (2003) *Annu Rev Biochem* 72, 609-642.
Kermani P., et al. (2005) *J Clin Invest* 115, 653-663.
Koda, M., et al. (2004) *J Neurotrauma* 21, 329-337.
Koyama, R., Ikegaya, Y. (2005) *The Neuroscientist* 11, 282-287.
Lebrun B. (2006) *Auton Neurosci.*, published online at the website for the Journal Autonomic Neuroscience on Apr. 21, 2006.

Lee, R., Kermani, P., Teng, K. K., Hempstead, B. L. (2001) Science 294, 1945-1948.
Lin, Y. Z., Yao, S. Y., Veach, R. A., Torgerson, T. R., Hawiger, J. (1995) J Biol Chem 270, 14255-14258.
Lipinski, C. A. (2000) J Pharm Toxicol Methods 44, 235-249.
Longo, F. M. et al. (1999) J Neurosci Res 55, 230-237.
Longo, F. M., Manthorpe, M., Xie, Y. M., Varon, S. (1997) J Neurosci Res 48, 1-17.
Lutz, M., and Kenakin, T. (1999) Quantitative Molecular Pharmacology and Informatics in Drug Discovery (Hoboken, N.J.: John Wiley & Sons).
Malcangio, Lessmann (2003) Trends in Pharm Sci 24, 116-121.
Massa, S. M., et al. (2006) J Neurosci 26, 5288-5300.
McGuinness, S. L., Shepherd, R. K. (2005) Otol Neurotol 26, 1064-1072.
Nakagawa, T., et al. (2003) Int J Obes Relat Metab Disord 27, 557-565.
Nomura, T., et al. (2005) Neurosci 136, 161-169.
Nosheny, R. L., et al., (2005) Neurotox Res 8, 187-198.
Nykjaer, A. et al., (2004) Nature 427, 843-848.
Nykjaer, A., Willnow, T. E., and Petersen, C. M. (2005) Curr Opin Neurobiol 15, 49-57.
Partridge, W. M. (2002) Adv Exp Med Bio 513, 397-430).
Podulso, J. F., Curran, G. L. (1996) Brain Res Mol Brain Res 36, 280-286.
Presgraves, S. P., et al. (2004) Exp Neurol 190, 157-170.
Remington: The Science and Practice of Pharmacy, A. Gennaro, ed., 20th edition, Lippincott, Williams & Wilkins, Philadelphia, Pa.
Remington's Pharmaceutical Sciences, Mack Pub. Co., Easton, Pa., 1980.
Sakurai, H., Chiba, H., Miyoshi, H., Sugita, T., Toriumi, W. (1999) J Biol Chem 274, 30353-30356.
Salehi, A. H., et al. (2000) Neuron 27, 279-288.
Saltzman, W. M., Mak, M. W., Mahoney, M. J., Duenas, E. T., Cleland, J. L. (1999) Pharm Res 16, 232-240.
Schabitz, W. E., et al. (2004) Stroke 35, 992-997.
Schechter, L. E., et al. (2005) NeuroRx 2, 590-611.
Stadelmann, C., et al., (2002) Brain 125, 75-85.
Sun, Y. E., Wu, H. (2006) Neuron 49, 321-323.
The BDNF Study Group, (1999) Neurology 52, 1427-1433.
Vogelin E., et al. (2006) Exp Neuro., published online on the website for the journal Experimental Neurology on Feb. 15, 2006.
Walsh, G. S., Krol, K. M., Kawaja, M. D. (1999) J Neurosci 19, 258-273.
Watabe, K., et al. (2005) Neuropath 25, 371-380.
Williams, G., et al. (2005) J Bio Chem 280, 5862-5869.
Wisse, B. E., Schwartz, M. W. (2003) Nat Neurosci 6, 655-656.
Wu, D. (2005) NeuroRx 2, 120-128.
Yang, T. et al. (2003) J Neurosci 23, 3353-3363.
Zhang, Y., et al. (2003) J Neurosci 23, 7385-7394.
Zhou, J., Holtzman, D. M., Weiner, R. I., Mobley, W. C. (1994) Proc Natl Acad Sci USA 91, 3824.
Zhou, J., Valletta, J. S., Grimes, M. L., Mobley, W. C. (1995) J Neurochem 65, 1146-1156.

It will be understood that various details of the presently claimed subject matter can be changed without departing from the scope of the presently claimed subject matter. Furthermore, the foregoing description is for the purpose of illustration only, and not for the purpose of limitation.

What is claimed is:

1. A method of treating a disorder in a subject in need thereof, comprising administering to the subject an effective amount of a compound represented by Formula (VII):

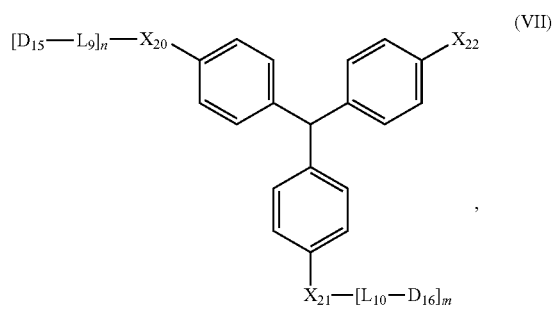

or a pharmaceutically acceptable salt thereof,
wherein:
  m and n are independently 2;
  each $L_9$ and $L_{10}$ is $C_1$-$C_5$ alkylene;
  $X_{20}$ and $X_{21}$ are N;
  $X_{22}$ is halo; and
  each $D_{15}$ and each $D_{16}$ are hydroxyl;
and
wherein the disorder is selected from the group consisting of Alzheimer's disease, Huntington's disease, amyotrophic lateral sclerosis, Rett syndrome, Parkinson's disease, spinal cord injury, stroke, ischemia, brain injury, motor neuron disease, multiple sclerosis, HIV dementia, peripheral nerve injury, hearing loss, and obesity.

2. The method of claim 1, wherein the subject is a human subject.

3. The method of claim 1, wherein the compound is represented by the structure:

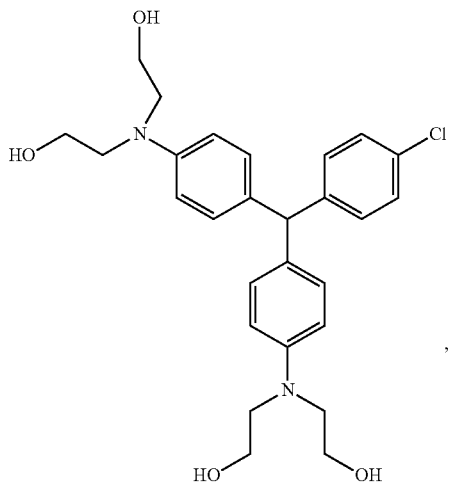 [SMILES: OCCN(CCO)c1ccc(C(c2ccc(Cl)cc2)c2ccc(N(CCO)CCO)cc2)cc1]

or a pharmaceutically acceptable salt thereof.

4. A method of facilitating neuronal or other cell survival, comprising contacting a cell with a compound represented by Formula (VII):

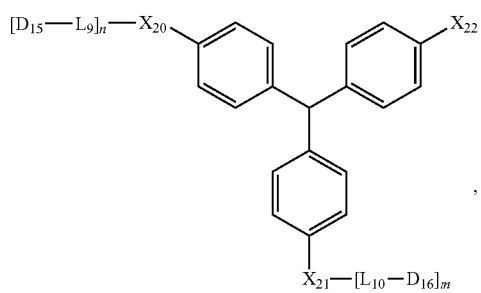

(VII)

or a pharmaceutically acceptable salt thereof, wherein:
  m and n are independently 2;
  each $L_9$ and $L_{10}$ is $C_1$-$C_5$ alkylene;
  $X_{20}$ and $X_{21}$ are N;
  $X_{22}$ is halo; and
  each $D_{15}$ and each $D_{16}$ are hydroxyl.

5. The method of claim 4, wherein the compound is represented by the structure:

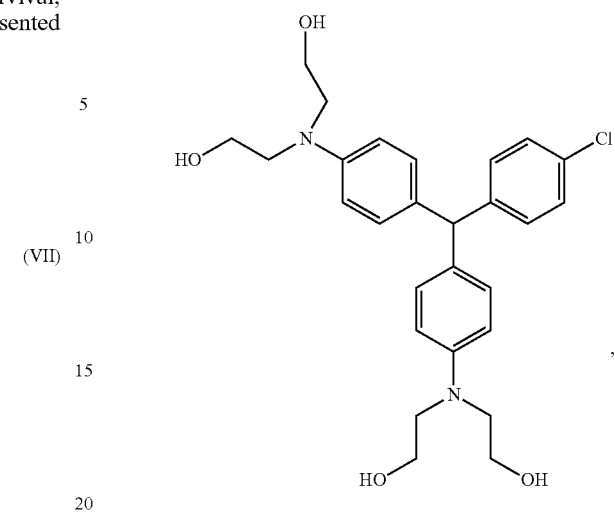

or a pharmaceutically acceptable salt thereof.

6. The method of claim 4, wherein the contacting is done in vitro.

7. The method of claim 1, wherein the compound is formulated in a unit dosage form comprising said compound and a pharmaceutically acceptable carrier.

8. The method of claim 4, wherein the compound is formulated in a unit dosage form comprising said compound and a pharmaceutically acceptable carrier.

9. The method of claim 1 or 4, wherein each $L_9$ and each $L_{10}$ are $C_1$-$C_3$ alkylene.

10. The method of claim 8, wherein each $L_9$ and each $L_{10}$ are $C_2$ alkylene.

11. The method of claim 1, wherein the disorder is selected from the group consisting of Alzheimer's disease, Huntington's disease, Rett syndrome, stroke, multiple sclerosis, and Parkinson's disease.

* * * * *